United States Patent
Atkinson et al.

(10) Patent No.: US 10,059,699 B2
(45) Date of Patent: Aug. 28, 2018

(54) TETRAHYDROQUINOLINE DERIVATIVES AS BROMODOMAIN INHIBITORS

(71) Applicant: GlaxoSmithKline Intellectual Property (No.2) Limited, Brentford, Middlesex (GB)

(72) Inventors: Stephen John Atkinson, Stevenage (GB); David Jonathan Hirst, Stevenage (GB); Philip G. Humphreys, Stevenage (GB); Matthew J. Lindon, Stevenage (GB); Alexander G. Preston, Stevenage (GB); Jonathan Thomas Seal, Stevenage (GB); Christopher Roland Wellaway, Stevenage (GB)

(73) Assignee: GlaxoSmithKline Intellectual Property (No.2) Limited, Brentford, Middlesex (GB)

( * ) Notice: Subject to any disclaimer, the term of this patent is extended or adjusted under 35 U.S.C. 154(b) by 0 days.

(21) Appl. No.: 15/509,894

(22) PCT Filed: Sep. 9, 2015

(86) PCT No.: PCT/EP2015/070665
§ 371 (c)(1),
(2) Date: Mar. 9, 2017

(87) PCT Pub. No.: WO2016/038120
PCT Pub. Date: Mar. 17, 2016

(65) Prior Publication Data
US 2017/0298047 A1    Oct. 19, 2017

Related U.S. Application Data

(60) Provisional application No. 62/049,449, filed on Sep. 12, 2014.

(51) Int. Cl.
*C07D 405/14* (2006.01)
*C07D 401/12* (2006.01)

(52) U.S. Cl.
CPC ......... *C07D 405/14* (2013.01); *C07D 401/12* (2013.01)

(58) Field of Classification Search
CPC ........................... C07D 405/14; C07D 401/12
See application file for complete search history.

(56) References Cited

U.S. PATENT DOCUMENTS 9,637,456 B2 *  5/2017  Amans ................ C07D 401/14
2012/0004197 A1  1/2012  Ashikawa et al.

FOREIGN PATENT DOCUMENTS

| WO |    2011054848 A1 | 5/2011 |
|----|------------------|--------|
| WO | WO 2011/054841 A1 | 5/2011 |
| WO | WO 2011/054843 A1 | 5/2011 |
| WO | WO 2012/143413 A1 | 10/2012 |
| WO | WO 2012/143415 A1 | 10/2012 |
| WO | WO 2012/150234 A1 | 11/2012 |
| WO |    2014140076 A1 | 9/2014 |

* cited by examiner

*Primary Examiner* — D Margaret M Seaman
(74) *Attorney, Agent, or Firm* — Duke M. Fitch; Kathryn A. Lutomski; Edward R. Gimmi

(57) ABSTRACT

The present invention relates to specific novel compounds, pharmaceutical compositions containing such compounds and to their use in therapy as bromodomain inhibitors.

18 Claims, No Drawings

TETRAHYDROQUINOLINE DERIVATIVES AS BROMODOMAIN INHIBITORS

This application is a § 371 of International Application No. PCT/EP2015/070665, filed 09 Sep. 2015, which claims the benefit of U.S. Provisional Application No. 62/049,449, filed 12 Sep. 2014, which are incorporated herein in their entireties.

FIELD OF THE INVENTION

The present invention relates to novel compounds, pharmaceutical compositions containing such compounds and to their use in therapy.

BACKGROUND OF THE INVENTION

The genomes of eukaryotic organisms are highly organised within the nucleus of the cell. The long strands of duplex DNA are wrapped around an octomer of histone proteins (most usually comprising two copies of histones H2A, H2B, H3 and H4) to form a nucleosome. This basic unit is then further compressed by the aggregation and folding of nucleosomes to form a highly condensed chromatin structure. A range of different states of condensation are possible, and the tightness of this structure varies during the cell cycle, being most compact during the process of cell division. Chromatin structure plays a critical role in regulating gene transcription, which cannot occur efficiently from highly condensed chromatin. The chromatin structure is controlled by a series of post translational modifications to histone proteins, notably histones H3 and H4, and most commonly within the histone tails which extend beyond the core nucleosome structure. These modifications include acetylation, methylation, phosphorylation, ubiquitinylation, SUMOylation. These epigenetic marks are written and erased by specific enzymes, which place the tags on specific residues within the histone tail, thereby forming an epigenetic code, which is then interpreted by the cell to allow gene specific regulation of chromatin structure and thereby transcription.

Histone acetylation is most usually associated with the activation of gene transcription, as the modification loosens the interaction of the DNA and the histone octomer by changing the electrostatics. In addition to this physical change, specific proteins recognise and bind to acetylated lysine residues within histones to read the epigenetic code. Bromodomains are small (~110 amino acid) distinct domains within proteins that bind to acetylated lysine residues commonly but not exclusively in the context of histones. There is a family of around 50 proteins known to contain bromodomains, and they have a range of functions within the cell.

The BET family of bromodomain containing proteins comprises 4 proteins (BRD2, BRD3, BRD4 and BRDT) which contain tandem bromodomains capable of binding to two acetylated lysine residues in close proximity, increasing the specificity of the interaction. Numbering from the N-terminal end of each BET protein the tandem bromodomains are typically labelled Binding Domain 1 (BD1) and Binding Domain 2 (BD2) (Chung et al, *J Med. Chem.*, 2011, 54, 3827-3838).

Funabashi et al describe 1,2,3,4,-tetrahydroquinolines and conduct a configuration and conformation analysis (Funabashi et al, *Bulletin of the Chemical Society of Japan*, 1969, 42, 2885-2894).

Patent applications WO2011/054841, WO2011/054848, WO2012/143413, WO2012/143415, WO2012/150234 and PCT/EP2014/054795 (published as WO2014/140076) describe series of tetrahydroquinoline derivatives as bromodomain inhibitors.

Further tetrahydroquinoline derivatives have been found which inhibit the binding of bromodomains with its cognate acetylated proteins, more particularly compounds that inhibit the binding of BET family bromodomains to aceylated lysine residues (hereafter be referred to as "bromodomain inhibitors") and which are believed to have one or more property that may make them particularly suitable for development as a pharmaceutical product.

SUMMARY OF THE INVENTION

In a first aspect of the present invention, there is provided a compound selected from the group consisting of:
1-acetyl-4-((5-cyanopyridin-2-yl)amino)-N-ethyl-2,3-dimethyl-1,2,3,4-tetrahydroquinoline-6-carboxamide;
1-acetyl-4-((5-cyanopyridin-2-yl)amino)-2,3-dimethyl-1,2,3,4-tetrahydroquinoline-6-carboxamide;
1-acetyl-4-((5-cyanopyridin-2-yl)amino)-2,3-dimethyl-N-(tetrahydro-2H-pyran-4-yl)-1,2,3,4-tetrahydroquinoline-6-carboxamide;
1-acetyl-4-((5-cyanopyridin-2-yl)amino)-N—((R)-2-hydroxypropyl)-2,3-dimethyl-1,2,3,4-tetrahydroquinoline-6-carboxamide;
1-acetyl-4-((5-cyanopyridin-2-yl)amino)-N—((S)-2-hydroxypropyl)-2,3-dimethyl-1,2,3,4-tetrahydroquinoline-6-carboxamide;
1-acetyl-4-((5-chloropyrimidin-2-yl)amino)-N-ethyl-2,3-dimethyl-1,2,3,4-tetrahydroquinoline-6-carboxamide;
1-acetyl-4-((5-chloropyrimidin-2-yl)amino)-2,3-dimethyl-1,2,3,4-tetrahydroquinoline-6-carboxamide;
1-acetyl-4-((5-chloropyrimidin-2-yl)amino)-2,3-dimethyl-N-(tetrahydro-2H-pyran-4-yl)-1,2,3,4-tetrahydroquinoline-6-carboxamide;
1-acetyl-4-((5-chloropyrimidin-2-yl)amino)-N—((S)-2-hydroxypropyl)-2,3-dimethyl-1,2,3,4-tetrahydroquinoline-6-carboxamide;
1-acetyl-4-((5-chloropyrimidin-2-yl)amino)-N—((R)-2-hydroxypropyl)-2,3-dimethyl-1,2,3,4-tetrahydroquinoline-6-carboxamide;
1-acetyl-4-((5-cyanopyrazin-2-yl)amino)-2,3-dimethyl-1,2,3,4-tetrahydroquinoline-6-carboxamide;
1-acetyl-4-((5-cyanopyrazin-2-yl)amino)-N-ethyl-2,3-dimethyl-1,2,3,4-tetrahydroquinoline-6-carboxamide;
1-acetyl-N-ethyl-4-((5-fluoropyridin-2-yl)amino)-2,3-dimethyl-1,2,3,4-tetrahydroquinoline-6-carboxamide;
1-acetyl-4-((5-chloropyrimidin-2-yl)amino)-2-methyl-1,2,3,4-tetrahydroquinoline-6-carboxamide;
1-acetyl-4-((5-chloropyrimidin-2-yl)amino)-N-ethyl-2-methyl-1,2,3,4-tetrahydroquinoline-6-carboxamide; and
1-acetyl-4-((5-cyanopyridin-2-yl)amino)-N-ethyl-2-methyl-1,2,3,4-tetrahydroquinoline-6-carboxamide or a salt thereof, more particularly a pharmaceutically acceptable salt thereof.

In a second aspect of the present invention, there is provided a pharmaceutical composition comprising a compound or a pharmaceutically acceptable salt thereof of the first aspect of the invention and one or more pharmaceutically acceptable carriers, diluents or excipients.

In a third aspect of the present invention, there is provided a compound or a pharmaceutically acceptable salt thereof of the first aspect of the invention for use in therapy, in particular in the treatment of diseases or conditions for which a bromodomain inhibitor is indicated.

In a fourth aspect of the present invention, there is provided a method of treating diseases or conditions for which a bromodomain inhibitor is indicated in a subject in need thereof which comprises administering a therapeutically effective amount of a compound or a pharmaceutically acceptable salt thereof of the first aspect of the invention.

In a fifth aspect of the present invention, there is provided the use of a compound or a pharmaceutically acceptable salt thereof of the first aspect of the invention in the manufacture of a medicament for the treatment of diseases or conditions for which a bromodomain inhibitor is indicated.

DETAILED DESCRIPTION OF THE INVENTION

In a first aspect, the present invention relates to a compound selected from the group consisting of a compound of formula (I), (II), (III), (IV), (V), (VI), (VII), (VIII), (IX), (X), (XI), (XII), (XIII), (XIV), (XV) and (XVI)

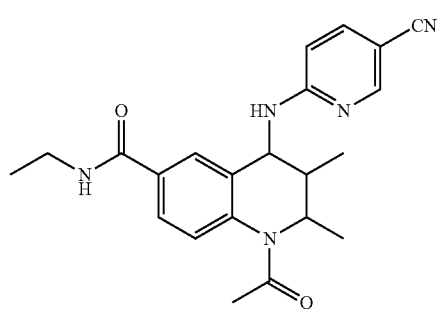

(I)

1-acetyl-4-((5-cyanopyridin-2-yl)amino)-N-ethyl-2,3-dimethyl-1,2,3,4-tetrahydroquinoline-6-carboxamide (compound of formula (I))

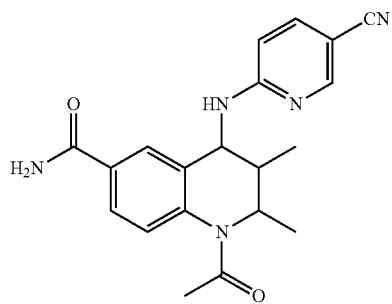

(II)

1-acetyl-4-((5-cyanopyridin-2-yl)amino)-2,3-dimethyl-1,2,3,4-tetrahydroquinoline-6-carboxamide (compound of formula (II))

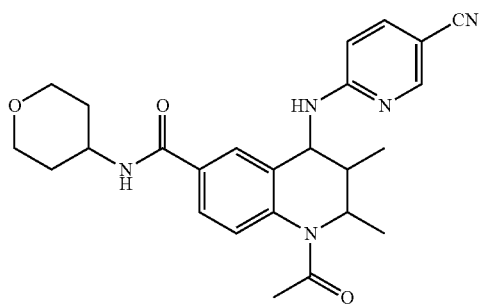

(III)

1-acetyl-4-((5-cyanopyridin-2-yl)amino)-2,3-dimethyl-N-(tetrahydro-2H-pyran-4-yl)-1,2,3,4-tetrahydroquinoline-6-carboxamide (compound of formula (III))

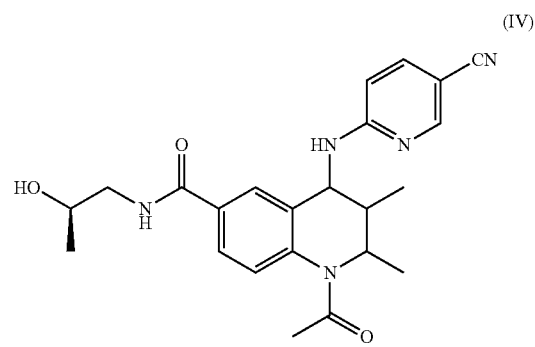

(IV)

1-acetyl-4-((5-cyanopyridin-2-yl)amino)-N-((R)-2-hydroxypropyl-2,3-dimethyl-1,2,3,4-tetrahydroquinoline-6-carboxamide (compound of formula (IV))

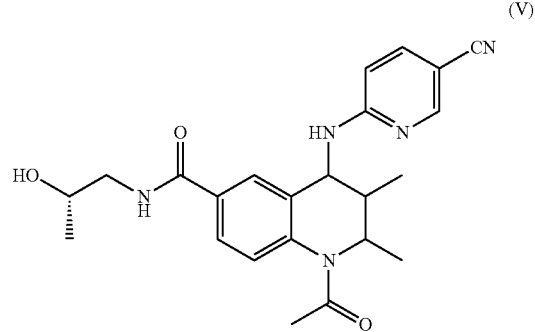

(V)

1-acetyl-4-((5-cyanopyridin-2-yl)amino)-N-((S)-2-hydroxypropyl-2,3-dimethyl-1,2,3,4-tetrahydroquinoline-6-carboxamide (compound of formula (V))

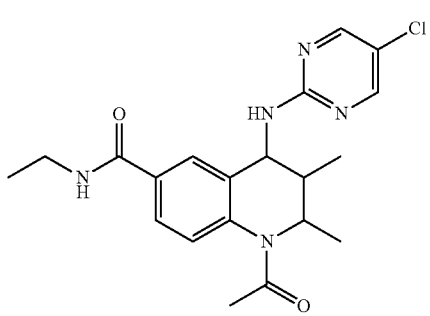

(VI)

1-acetyl-4-((5-chloropyrimidin-2-yl)amino)-N-ethyl-2,3-dimethyl-1,2,3,4-tetrahydroquinoline-6-carboxamide (compound of formula (VI))

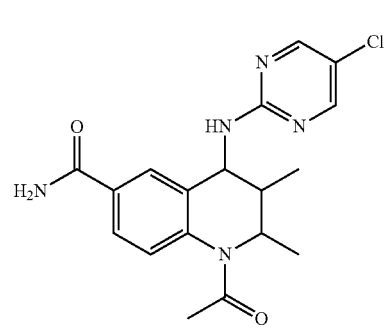

(VII)

1-acetyl-4-((5-chloropyrimidin-2-yl)amino)-2,3-dimethyl-1,2,3,4-tetrahydroquinoline-6-carboxamide (compound of formula (VII))

-continued

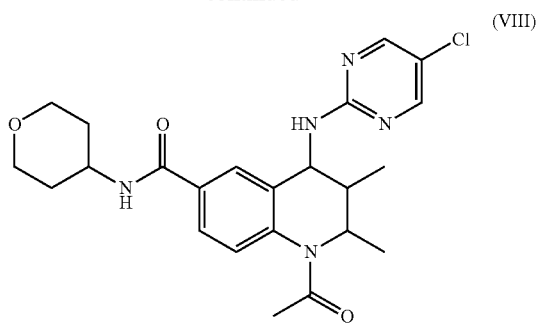

1-acetyl-4-((5-chloropyrimidin-2-yl)amino)-2,3-dimethyl-N-(tetrahydro-2H-pyran-4-yl)-1,2,3,4-tetrahydroquinoline-6-carboxamide (compound of formula (VIII))

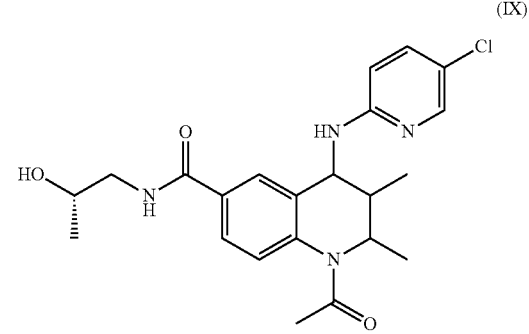

1-acetyl-4-((5-chloropyrimidin-2-yl)amino)-N-((S)-2-hydroxypropyl-2,3-dimethyl-1,2,3,4-tetrahydroquinoline-6-carboxamide (compound of formula (IX))

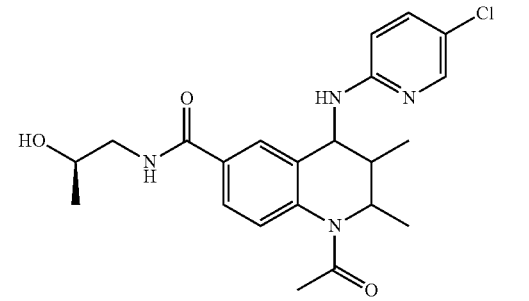

1-acetyl-4-((5-chloropyrimidin-2-yl)amino)-N-((R)-2-hydroxypropyl-2,3-dimethyl-1,2,3,4-tetrahydroquinoline-6-carboxamide (compound of formula (X))

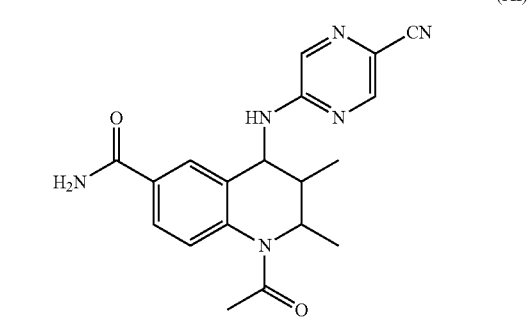

1-acetyl-4-((5-cyanopyrazin-2-yl)amino)-2,3-dimethyl-1,2,3,4-tetrahydroquinoline-6-carboxamide (compound of formula (XI))

-continued

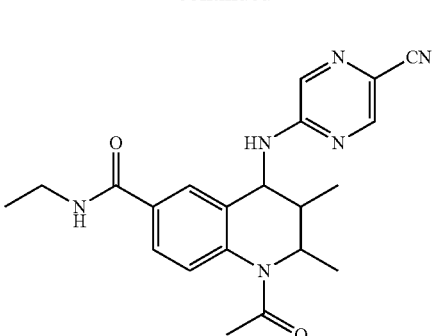

1-acetyl-4-((5-cyanopyrazin-2-yl)amino)-N-ethyl-2,3-dimethyl-1,2,3,4-tetrahydroquinoline-6-carboxamide (compound of formula (XII))

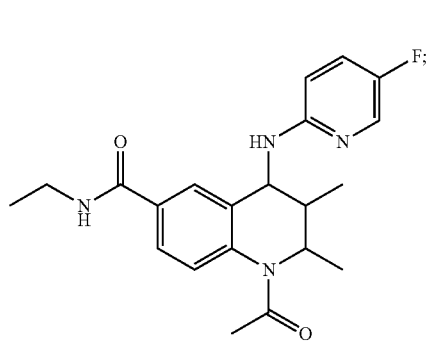

1-acetyl-N-ethyl-4-((5-fluoropyridin-2-yl)amino)-2,3-dimethyl-1,2,3,4-tetrahydroquinoline-6-carboxamide (compound of formula (XIII))

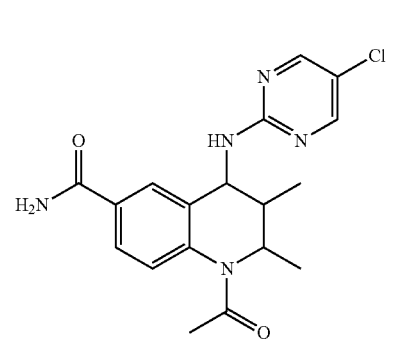

1-acetyl-4-((5-chloropyrimidin-2-yl)amino)-1,2,3,4-tetrahydroquinoline-6-carboxamide (compound of formula (XIV))

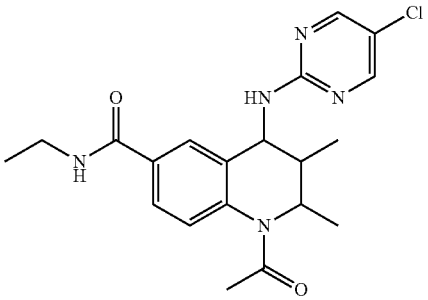

1-acetyl-4-((5-chloropyrimidin-2-yl)amino)-N-ethyl-2-methyl-1,2,3,4-tetrahydroquinoline-6-carboxamide (compound of formula (XV))

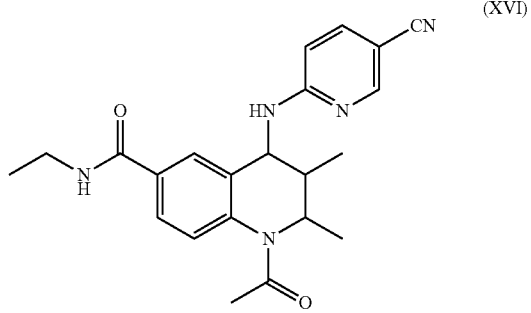

1-acetyl-4-((5-cyanopyridin-2-yl)amino)-N-ethyl-2-methyl-1,2,3,4-tetrahydroquinoline-6-carboxamide (compound of formula (XVI))

The compounds of formulae (I)-(XVI) contain at least 2 chiral atoms such that optical isomers, e.g. enantiomers and diastereomers may be formed. Accordingly, the present invention encompasses all isomers of the compounds of formulae (I)-(XVI) whether as individual isomers isolated such as to be substantially free of the other isomers (i.e. pure) or as mixtures (e.g. racemates or racemic mixtures). An individual isomer isolated such as to be substantially free of the other isomers (i.e. pure) may be isolated such that less than 10%, particularly less than about 1%, for example less than about 0.1% of the other isomers are present. Separation of isomers may be achieved by conventional techniques known to those skilled in the art, e.g. by fractional crystallisation, flash column chromatography or HPLC.

In one embodiment the present invention provides a compound of formula (Ia) which is (2S,3R,4R)-1-acetyl-4-((5-cyanopyridin-2-yl)amino)-N-ethyl-2,3-dimethyl-1,2,3,4-tetrahydroquinoline-6-carboxamide

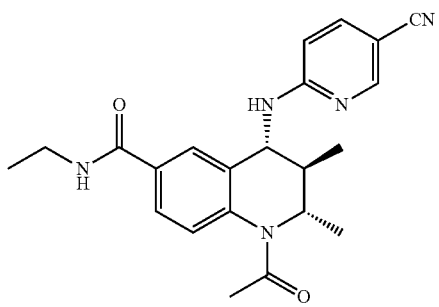

or a salt thereof.

In one embodiment the present invention provides a compound of formula (IIa) which is (2S,3R,4R)-1-acetyl-4-((5-cyanopyridin-2-yl)amino)-2,3-dimethyl-1,2,3,4-tetrahydroquinoline-6-carboxamide

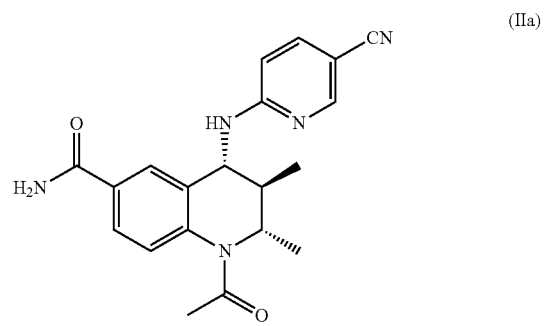 [SMILES: CC(=O)N1c2ccc(C(N)=O)cc2[C@H](Nc2ccc(C#N)cn2)[C@@H](C)[C@@H]1C]

or a salt thereof.

In one embodiment the present invention provides a compound of formula (IIIa) which is (2S,3R,4R)-1-acetyl-4-((5-cyanopyridin-2-yl)amino)-2,3-dimethyl-N-(tetrahydro-2H-pyran-4-yl)-1,2,3,4-tetrahydroquinoline-6-carboxamide

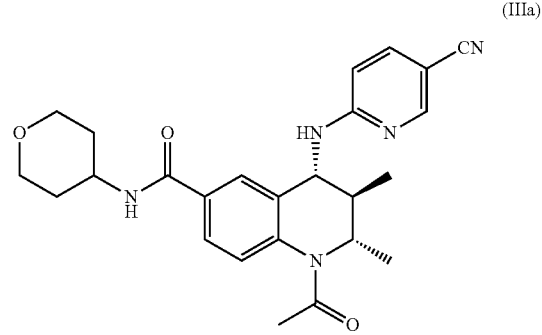 [SMILES: CC(=O)N1c2ccc(C(=O)NC3CCOCC3)cc2[C@H](Nc2ccc(C#N)cn2)[C@@H](C)[C@@H]1C]

or a salt thereof.

In one embodiment the present invention provides a compound of formula (IVa) which is (2S,3R,4R)-1-acetyl-4-((5-cyanopyridin-2-yl)amino)-N—((R)-2-hydroxypropyl)-2,3-dimethyl-1,2,3,4-tetrahydroquinoline-6-carboxamide

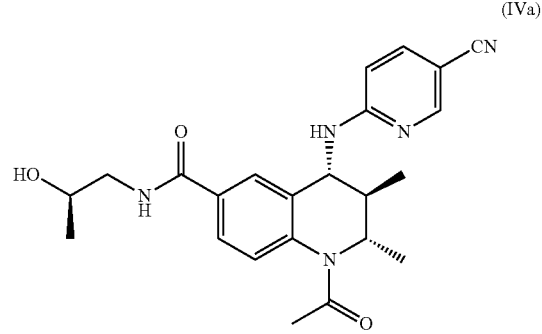 [SMILES: CC(=O)N1c2ccc(C(=O)NC[C@@H](C)O)cc2[C@H](Nc2ccc(C#N)cn2)[C@@H](C)[C@@H]1C]

or a salt thereof.

In one embodiment the present invention provides a compound of formula (Va) which is (2S,3R,4R)-1-acetyl-4-((5-cyanopyridin-2-yl)amino)-N—((S)-2-hydroxypropyl)-2,3-dimethyl-1,2,3,4-tetrahydroquinoline-6-carboxamide

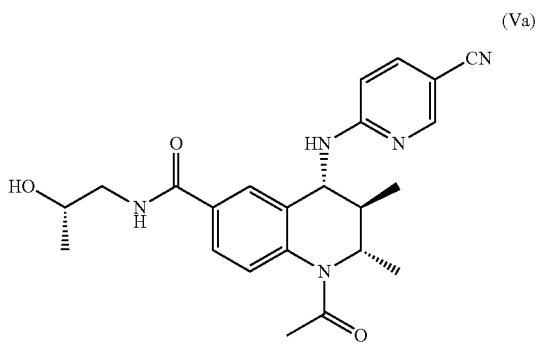 [SMILES: CC(=O)N1c2ccc(C(=O)NC[C@H](C)O)cc2[C@H](Nc2ccc(C#N)cn2)[C@@H](C)[C@@H]1C]

(Va)

or a salt thereof.

In one embodiment the present invention provides a compound of formula (VIa) which is (2S,3R,4R)-1-acetyl-4-((5-chloropyrimidin-2-yl)amino)-N-ethyl-2,3-dimethyl-1,2,3,4-tetrahydroquinoline-6-carboxamide

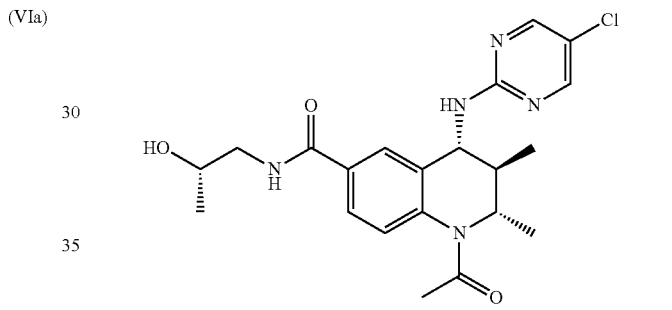

(VIa)

or a salt thereof.

In one embodiment the present invention provides a compound of formula (VIIa) which is (2S,3R,4R)-1-acetyl-4-((5-chloropyrimidin-2-yl)amino)-2,3-dimethyl-1,2,3,4-tetrahydroquinoline-6-carboxamide (VIIa)

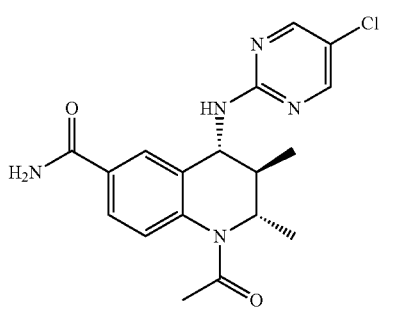

or a salt thereof.

In one embodiment the present invention provides a compound of formula (VIIIa) which is (2S,3R,4R)-1-acetyl-4-((5-chloropyrimidin-2-yl)amino)-2,3-dimethyl-N-(tetrahydro-2H-pyran-4-yl)-1,2,3,4-tetrahydroquinoline-6-carboxamide

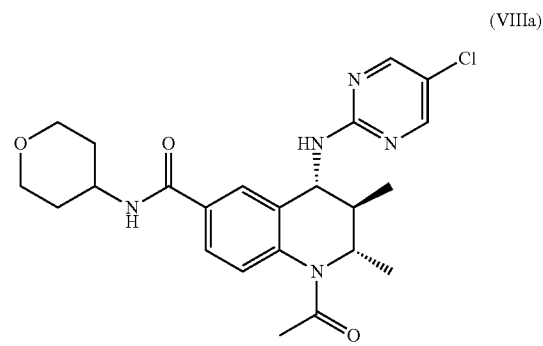 [SMILES: CC(=O)N1c2ccc(C(=O)NC3CCOCC3)cc2[C@H](Nc2ncc(Cl)cn2)[C@@H](C)[C@@H]1C]

(VIIIa)

or a salt thereof.

In one embodiment the present invention provides a compound of formula (IXa) which is (2S,3R,4R)-1-acetyl-4-((5-chloropyrimidin-2-yl)amino)-N—((S)-2-hydroxypropyl)-2,3-dimethyl-1,2,3,4-tetrahydroquinoline-6-carboxamide (IXa)

or a salt thereof.

In one embodiment the present invention provides a compound of formula (Xa) which is (2S,3R,4R)-1-acetyl-4-((5-chloropyrimidin-2-yl)amino)-N—((R)-2-hydroxypropyl)-2,3-dimethyl-1,2,3,4-tetrahydroquinoline-6-carboxamide (Xa)

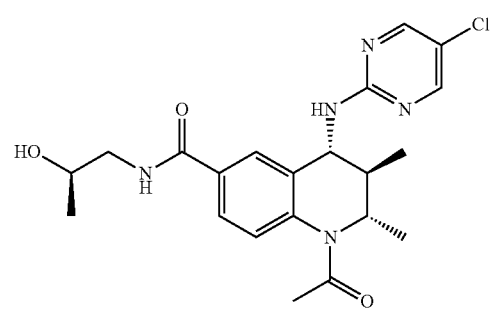

or a salt thereof.

In one embodiment the present invention provides a compound of formula (XIa) which is (2S,3R,4R)-1-acetyl-4-((5-cyanopyrazin-2-yl)amino)-2,3-dimethyl-1,2,3,4-tetrahydroquinoline-6-carboxamide

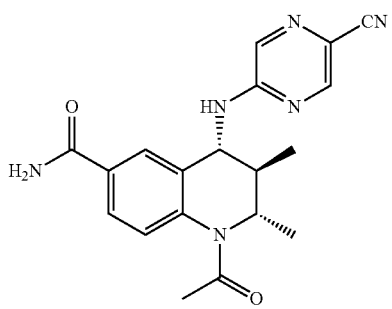

(XIa)

or a salt thereof.

In one embodiment the present invention provides a compound of formula (XIIa) which is (2S,3R,4R)-1-acetyl-4-((5-cyanopyrazin-2-yl)amino)-N-ethyl-2,3-dimethyl-1,2,3,4-tetrahydroquinoline-6-carboxamide

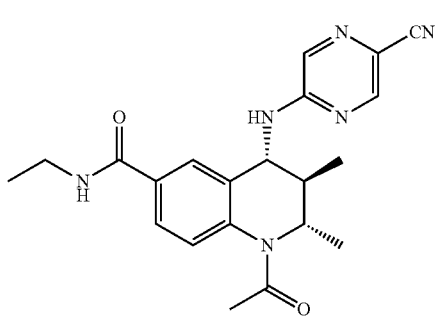

(XIIa)

or a salt thereof.

In one embodiment the present invention provides a compound of formula (XIIIa) which is (2S,3R,4R)-1-acetyl-N-ethyl-4-((5-fluoropyridin-2-yl)amino)-2,3-dimethyl-1,2,3,4-tetrahydroquinoline-6-carboxamide

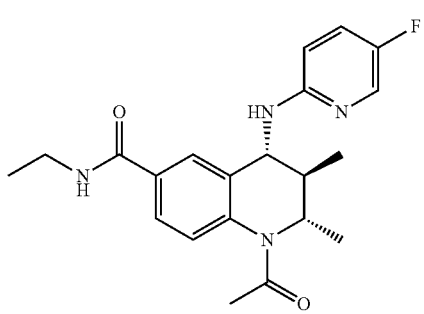

(XIIIa)

or a salt thereof.

In one embodiment the present invention provides a compound of formula (XIVa) which is (2S,4R)-1-acetyl-4-((5-chloropyrimidin-2-yl)amino)-2-methyl-1,2,3,4-tetrahydroquinoline-6-carboxamide

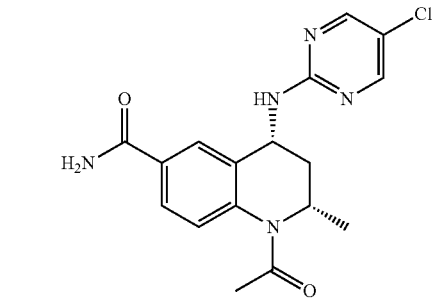

(XIVa)

or a salt thereof.

In one embodiment the present invention provides a compound of formula (XVa) which is (2S,4R)-1-acetyl-4-((5-chloropyrimidin-2-yl)amino)-N-ethyl-2-methyl-1,2,3,4-tetrahydroquinoline-6-carboxamide

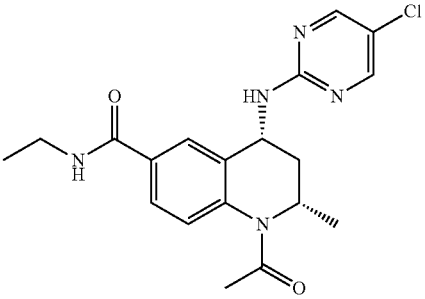

(XVa)

or a salt thereof.

In one embodiment the present invention provides a compound of formula (XVIa) which is (2S,4R)-1-acetyl-4-((5-cyanopyridin-2-yl)amino)-N-ethyl-2-methyl-1,2,3,4-tetrahydroquinoline-6-carboxamide

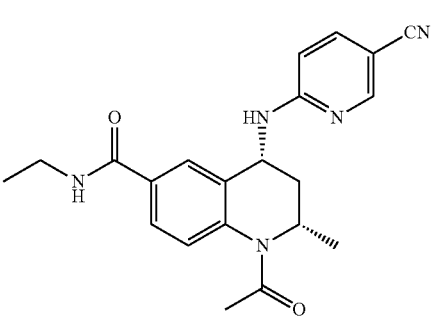

(XVIa)

or a salt thereof.

The term "pharmaceutically acceptable" refers to those compounds, materials, compositions, and dosage forms which are, within the scope of sound medical judgment, suitable for use in contact with the tissues of human beings and animals without excessive toxicity, irritation, or other problem or complication, commensurate with a reasonable benefit/risk ratio.

Where used herein the terms such as "a compound of formula (I)-(XVI)" and "compounds of formulae (I)-(XVI)" are intended to refer to each and all of the compounds as defined above i.e the compounds of formulae (I), (II), (Ill), (IV), (V), (VI), (VII), (VIII), (IX), (X), (XI), (XII), (XIII), (XIV), (XV) and (XVI) and also the compounds of formulae (Ia), (IIa), (IIIa), (IVa), (Va), (VIa), (VIIa), (VIIIa), (IXa), (Xa), (XIa), (XIIa), (XIIIa), (XIVa), (XVa) and (XVIa).

It will be appreciated that the present invention covers compounds of formulae (I)-(XVI) as the free base and as salts thereof, for example as a pharmaceutically acceptable salt thereof. In one embodiment the invention relates to compounds of formulae (I)-(XVI) in the form of a free base. In one embodiment the invention relates to compounds of formulae (I)-(XVI) or a pharmaceutically acceptable salt thereof.

Because of their potential use in medicine, salts of the compounds of formula (I)-(XVI) are desirably pharmaceutically acceptable. Suitable pharmaceutically acceptable salts can include acid addition salts. For a review of suitable pharmaceutically acceptable salts see Berge et al., *J. Pharm. Sci.*, 66:1-19, (1977). Typically, a pharmaceutically acceptable salt may be readily prepared by using a desired acid or base as appropriate. The resultant salt may precipitate from solution and be collected by filtration or may be recovered by evaporation of the solvent.

A pharmaceutically acceptable acid addition salt can be formed by reaction of a compound of formulae (I)-(XVI) with a suitable inorganic or organic acid (such as hydrobromic, hydrochloric, sulphuric, nitric, phosphoric, succinic, maleic, acetic, propionic, fumaric, citric, tartaric, lactic, benzoic, salicylic, aspartic, p-toluenesulphonic, benzenesulphonic, methanesulphonic, ethanesulphonic, naphthalenesulphonic such as 2-naphthalenesulphonic, or hexanoic acid), optionally in a suitable solvent such as an organic solvent, to give the salt which is usually isolated for example by crystallisation and filtration or by evaporation followed by trituration. A pharmaceutically acceptable acid addition salt of a compounds of formulae (I)-(XVI) can comprise or be for example a hydrobromide, hydrochloride, sulfate, nitrate, phosphate, succinate, maleate, acetate, propionate, fumarate, citrate, tartrate, lactate, benzoate, salicylate, glutamate, aspartate, p-toluenesulphonate, benzenesulphonate, methanesulphonate, ethanesulphonate, naphthalenesulphonate (e.g. 2-naphthalenesulphonate) or hexanoate salt.

Other non-pharmaceutically acceptable salts, e.g. formates, oxalates or trifluoroacetates, may be used, for example in the isolation of the compounds of formulae (I)-(XVI) and are included within the scope of this invention.

The invention includes within its scope all possible stoichiometric and non-stoichiometric forms of the salts of the compounds of formulae (I)-(XVI).

It will be appreciated that many organic compounds can form complexes with solvents in which they are reacted or from which they are precipitated or crystallised. These complexes are known as "solvates". For example, a complex with water is known as a "hydrate". Solvents with high boiling points and/or capable of forming hydrogen bonds such as water, xylene, N-methyl pyrrolidinone, methanol and ethanol may be used to form solvates. Methods for identification of solvates include, but are not limited to, NMR and microanalysis. Solvates of the compounds of formulae (I)-(XVI) are within the scope of the invention.

The invention includes within its scope all possible stoichiometric and non-stoichiometric forms of the solvates of the compounds of formulae (I)-(XVI).

The invention encompasses all prodrugs, of the compounds of formulae (I)-(XVI) or a pharmaceutically acceptable salt thereof, which upon administration to the recipient is capable of providing (directly or indirectly) the compounds of formulae (I)-(XVI) or a pharmaceutically acceptable salt thereof, or an active metabolite or residue thereof. Such derivatives are recognisable to those skilled in the art, without undue experimentation. Nevertheless, reference is made to the teaching of Burger's Medicinal Chemistry and Drug Discovery, 5th Edition, Vol 1: Principles and Practice, which is incorporated herein by reference to the extent of teaching such derivatives.

The compounds of formulae (I)-(XVI) may be in crystalline or amorphous form. Furthermore, some of the crystalline forms of the compounds of formulae (I)-(XVI) may exist as polymorphs, which are included within the scope of the present invention. Such polymorphic forms may be characterized and differentiated using a number of conventional analytical techniques, including, but not limited to, X-ray powder diffraction (XRPD) patterns, infrared (IR) spectra, Raman spectra, differential scanning calorimetry (DSC), thermogravimetric analysis (TGA) and solid state nuclear magnetic resonance (SSNMR).

It will be appreciated from the foregoing that included within the scope of the invention are solvates, isomers and polymorphic forms of the compounds of formulae (I)-(XVI) and salts thereof.

The compounds of formulae (I)-(XVI) or salts thereof may be prepared by a variety of methods, particularly those described herein.

It will be appreciated by those skilled in the art that during such syntheses it may be advantageous to protect one or more functional groups of the compounds described above. Examples of protecting groups and the means for their removal can be found in T. W. Greene 'Protective Groups in Organic Synthesis' (4th edition, J. Wiley and Sons, 2006). Suitable amine protecting groups include acyl (e.g. acetyl, carbamate (e.g. 2',2',2'-trichloroethoxycarbonyl, benzyloxycarbonyl or t-butoxycarbonyl) and arylalkyl (e.g. benzyl), which may be removed by hydrolysis (e.g. using an acid such as hydrochloric acid in 1,4-dioxane or trifluoroacetic acid in dichloromethane) or reductively (e.g. hydrogenolysis of a benzyl or benzyloxycarbonyl group or reductive removal of a 2',2',2'-trichloroethoxycarbonyl group using zinc in acetic acid) as appropriate. Other suitable amine protecting groups include trifluoroacetyl (—COCF$_3$) which may be removed by base catalysed hydrolysis.

It will also be appreciated that the precise order of the synthetic steps by which the various groups and moieties are introduced into the molecule may be varied. It will be within the skill of the practitioner in the art to ensure that groups or moieties introduced at one stage of the process will not be affected by subsequent transformations and reactions, and to select the order of synthetic steps accordingly.

The compound (2S,4R)-1-acetyl-4-((5-chloropyrimidin-2-yl)amino)-2-methyl-1,2,3,4-tetrahydroquinoline-6-carboxamide may also be prepared by a method described in Scheme 1 below.

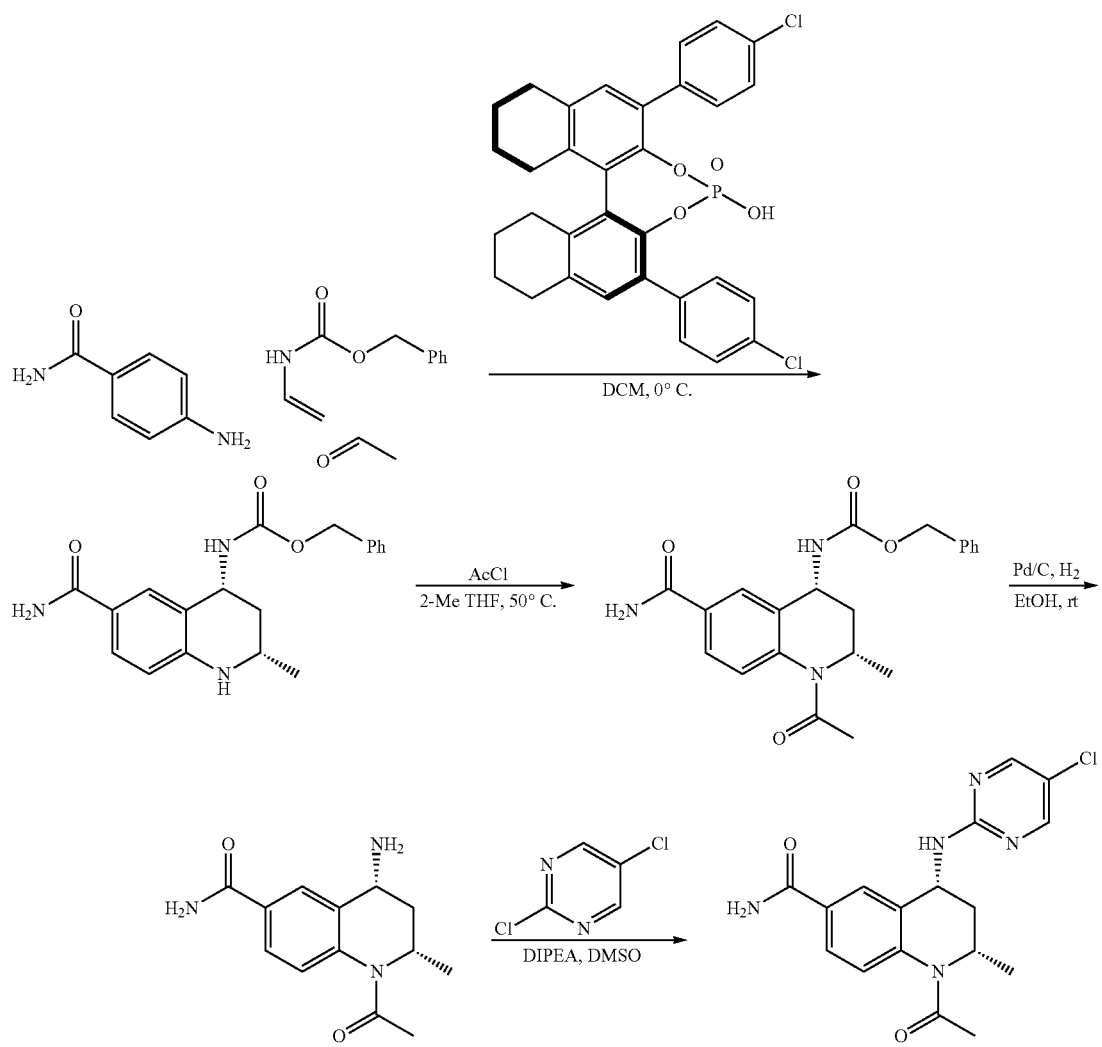

Scheme 1

Compounds of formula (I)-(XVI) or a pharmaceutically acceptable salt thereof may show an improved profile over known BET inhibitors in that they may possess, for example, one or more of the following properties:
(i) potent BET inhibitory activity;
(ii) selectivity over other known bromodomain containing proteins outside of the BET family of proteins; or
(iii) a suitable developability profile (e.g. suitable solubility, drug-drug interaction profile, in vitro toxicology profile and pharmacokinetics/pharmacodynamics).

Certain compounds disclosed herein may possess a combination of the above properties which make them particularly suitable for oral administration in humans. For example, the compound of formula (XIVa) has been found to show no cytochrome P450 3A4 metabolism dependent inhibition, no hERG liability and may have a profile which supports once a day or intermittent oral dosing in humans.

The compounds of formulae (I)-(XVI) and pharmaceutically acceptable salts thereof are believed to have potential utility in the treatment of a number of diseases or conditions. The compounds of formulae (I)-(XVI) or a pharmaceutically acceptable salt thereof are bromodomain inhibitors and can thereof be used in the treatment of diseases or conditions for which a bromodomain inhibitor is indicated.

In a further aspect the present invention provides a compound of formula (I)-(XVI) or a pharmaceutically acceptable salt thereof for use in therapy, in particular in the treatment of diseases or conditions for which a bromodomain inhibitor is indicated.

In one embodiment the present invention provides a compound (2S,3R,4R)-1-acetyl-4-((5-cyanopyridin-2-yl)amino)-N-ethyl-2,3-dimethyl-1,2,3,4-tetrahydroquinoline-6-carboxamide or a pharmaceutically acceptable salt thereof for use in therapy, in particular in the treatment of diseases or conditions for which a bromodomain inhibitor is indicated.

In one embodiment the present invention provides a compound (2S,3R,4R)-1-acetyl-4-((5-cyanopyridin-2-yl)amino)-2,3-dimethyl-1,2,3,4-tetrahydroquinoline-6-carboxamide or a pharmaceutically acceptable salt thereof for use in therapy, in particular in the treatment of diseases or conditions for which a bromodomain inhibitor is indicated.

In one embodiment the present invention provides a compound (2S,3R,4R)-1-acetyl-4-((5-cyanopyridin-2-yl)amino)-2,3-dimethyl-N-(tetrahydro-2H-pyran-4-yl)-1,2,3,4-tetrahydroquinoline-6-carboxamide or a pharmaceutically acceptable salt thereof for use in therapy, in particular in the treatment of diseases or conditions for which a bromodomain inhibitor is indicated.

In one embodiment the present invention provides a compound (2S,3R,4R)-1-acetyl-4-((5-cyanopyridin-2-yl)amino)-N—((R)-2-hydroxypropyl)-2,3-dimethyl-1,2,3,4-tetrahydroquinoline-6-carboxamide or a pharmaceutically acceptable salt thereof for use in therapy, in particular in the treatment of diseases or conditions for which a bromodomain inhibitor is indicated.

In one embodiment the present invention provides a compound (2S,3R,4R)-1-acetyl-4-((5-cyanopyridin-2-yl)amino)-N—((S)-2-hydroxypropyl)-2,3-dimethyl-1,2,3,4-tetrahydroquinoline-6-carboxamide or a pharmaceutically acceptable salt thereof for use in therapy, in particular in the treatment of diseases or conditions for which a bromodomain inhibitor is indicated.

In one embodiment the present invention provides a compound (2S,3R,4R)-1-acetyl-4-((5-chloropyrimidin-2-yl)amino)-N-ethyl-2,3-dimethyl-1,2,3,4-tetrahydroquinoline-6-carboxamide or a pharmaceutically acceptable salt thereof for use in therapy, in particular in the treatment of diseases or conditions for which a bromodomain inhibitor is indicated.

In one embodiment the present invention provides a compound (2S,3R,4R)-1-acetyl-4-((5-chloropyrimidin-2-yl)amino)-2,3-dimethyl-1,2,3,4-tetrahydroquinoline-6-carboxamide or a pharmaceutically acceptable salt thereof for use in therapy, in particular in the treatment of diseases or conditions for which a bromodomain inhibitor is indicated.

In one embodiment the present invention provides a compound (2S,3R,4R)-1-acetyl-4-((5-chloropyrimidin-2-yl)amino)-2,3-dimethyl-N-(tetrahydro-2H-pyran-4-yl)-1,2,3,4-tetrahydroquinoline-6-carboxamide or a pharmaceutically acceptable salt thereof for use in therapy, in particular in the treatment of diseases or conditions for which a bromodomain inhibitor is indicated.

In one embodiment the present invention provides a compound (2S,3R,4R)-1-acetyl-4-((5-chloropyrimidin-2-yl)amino)-N—((S)-2-hydroxypropyl)-2,3-dimethyl-1,2,3,4-tetrahydroquinoline-6-carboxamide or a pharmaceutically acceptable salt thereof for use in therapy, in particular in the treatment of diseases or conditions for which a bromodomain inhibitor is indicated.

In one embodiment the present invention provides a compound (2S,3R,4R)-1-acetyl-4-((5-chloropyrimidin-2-yl)amino)-N—((R)-2-hydroxypropyl)-2,3-dimethyl-1,2,3,4-tetrahydroquinoline-6-carboxamide or a pharmaceutically acceptable salt thereof for use in therapy, in particular in the treatment of diseases or conditions for which a bromodomain inhibitor is indicated.

In one embodiment the present invention provides a compound (2S,3R,4R)-1-acetyl-4-((5-cyanopyrazin-2-yl)amino)-2,3-dimethyl-1,2,3,4-tetrahydroquinoline-6-carboxamide or a pharmaceutically acceptable salt thereof for use in therapy, in particular in the treatment of diseases or conditions for which a bromodomain inhibitor is indicated.

In one embodiment the present invention provides a compound (2S,3R,4R)-1-acetyl-4-((5-cyanopyrazin-2-yl)amino)-N-ethyl-2,3-dimethyl-1,2,3,4-tetrahydroquinoline-6-carboxamide or a pharmaceutically acceptable salt thereof for use in therapy, in particular in the treatment of diseases or conditions for which a bromodomain inhibitor is indicated.

In one embodiment the present invention provides a compound (2S,3R,4R)-1-acetyl-N-ethyl-4-((5-fluoropyridin-2-yl)amino)-2,3-dimethyl-1,2,3,4-tetrahydroquinoline-6-carboxamide or a pharmaceutically acceptable salt thereof for use in therapy, in particular in the treatment of diseases or conditions for which a bromodomain inhibitor is indicated.

In one embodiment the present invention provides a compound (2S,4R)-1-acetyl-4-((5-chloropyrimidin-2-yl)amino)-2-methyl-1,2,3,4-tetrahydroquinoline-6-carboxamide or a pharmaceutically acceptable salt thereof for use in therapy, in particular in the treatment of diseases or conditions for which a bromodomain inhibitor is indicated.

In one embodiment the present invention provides a compound (2S,4R)-1-acetyl-4-((5-chloropyrimidin-2-yl)amino)-N-ethyl-2-methyl-1,2,3,4-tetrahydroquinoline-6-carboxamide or a pharmaceutically acceptable salt thereof for use in therapy, in particular in the treatment of diseases or conditions for which a bromodomain inhibitor is indicated.

In one embodiment the present invention provides a compound (2S,4R)-1-acetyl-4-((5-cyanopyridin-2-yl)amino)-N-ethyl-2-methyl-1,2,3,4-tetrahydroquinoline-6-carboxamide or a pharmaceutically acceptable salt thereof for use in therapy, in particular in the treatment of diseases or conditions for which a bromodomain inhibitor is indicated.

In one embodiment there is provided a compound of formula (I)-(XVI) or a pharmaceutically acceptable salt thereof for use in the treatment of acute or chronic auto-immune and/or inflammatory conditions.

In another embodiment there is provided a compound of formula (I)-(XVI) or a pharmaceutically acceptable salt thereof for use in the treatment of diseases or conditions which involve inflammatory responses to infections with bacteria, viruses, fungi, parasites or their toxins.

In another embodiment there is provided a compound of formula (I)-(XVI) or a pharmaceutically acceptable salt thereof for use in the treatment of viral infections.

In another embodiment there is provided a compound of formula (I)-(XVI) or a pharmaceutically acceptable salt thereof for use in the treatment of cancer.

Also provided is the use of a compound of formula (I)-(XVI) or a pharmaceutically acceptable salt thereof in the manufacture of a medicament for the treatment of diseases or conditions for which a bromodomain inhibitor is indicated.

In one embodiment there is provided the use of a compound of formula (I)-(XVI) or a pharmaceutically acceptable salt thereof in the manufacture of a medicament for the treatment of acute or chronic auto-immune and/or inflammatory conditions. In another embodiment there is provided the use of a compound of formula (I)-(XVI) or a pharmaceutically acceptable salt thereof in the manufacture of a medicament for the treatment of diseases or conditions which involve inflammatory responses to infections with bacteria, viruses, fungi, parasites or their toxins. In another embodiment there is provided the use of a compound of formula (I)-(XVI) or a pharmaceutically acceptable salt thereof in the manufacture of a medicament for the treatment of viral infections. In another embodiment there is provided the use of a compound of formula (I)-(XVI) or a pharmaceutically acceptable salt thereof in the manufacture of a medicament for the treatment of cancer.

Also provided is a method of treating diseases or conditions for which a bromodomain inhibitor is indicated in a subject in need thereof which comprises administering a therapeutically effective amount of a compound of formula (I)-(XVI) or a pharmaceutically acceptable salt thereof. In one embodiment the subject is a human.

In one embodiment there is provided a method of treating acute or chronic auto-immune and/or inflammatory conditions in a subject in need thereof which comprises administering a therapeutically effective amount of a compound of formula (I)-(XVI) or a pharmaceutically acceptable salt thereof. In another embodiment there is provided a method of treating diseases or conditions which involve inflammatory responses to infections with bacteria, viruses, fungi, parasites or their toxins in a subject in need thereof which comprises administering a therapeutically effective amount of a compound of formula (I) or a pharmaceutically acceptable salt thereof. In another embodiment there is provided a method of treating viral infections in a subject in need thereof which comprises administering a therapeutically effective amount of a compound of formula (I)-(XVI) or a pharmaceutically acceptable salt thereof. In further embodiment there is provided a method of treating cancer in a subject in need thereof which comprises administering a therapeutically effective amount of a compound of formula (I)-(XVI) or a pharmaceutically acceptable salt thereof. In a particular embodiment there is provided a method of treating cancer in a subject in need thereof which comprises administering a therapeutically effective amount of a compound of formula (XIVa), that is to say (2S,4R)-1-acetyl-4-((5-chloropyrimidin-2-yl)amino)-2-methyl-1,2,3,4-tetrahydroquinoline-6-carboxamide, or a pharmaceutically acceptable salt thereof.

Bromodomain inhibitors are believed to be useful in the treatment of a variety of diseases or conditions related to systemic or tissue inflammation, inflammatory responses to infection or hypoxia, cellular activation and proliferation, lipid metabolism, fibrosis and in the prevention and treatment of viral infections.

Bromodomain inhibitors may be useful in the treatment of a wide variety of acute or chronic autoimmune and/or inflammatory conditions such as rheumatoid arthritis, osteoarthritis, acute gout, psoriasis, systemic lupus erythematosus, multiple sclerosis, inflammatory bowel disease (Crohn's disease and Ulcerative colitis), asthma, chronic obstructive airways disease, pneumonitis, myocarditis, pericarditis, myositis, eczema, dermatitis (including atopic dermatitis), alopecia, vitiligo, bullous skin diseases, nephritis, vasculitis, hypercholesterolemia, atherosclerosis, Alzheimer's disease, depression, Sjögren's syndrome, sialoadenitis, central retinal vein occlusion, branched retinal vein occlusion, Irvine-Gass syndrome (post cataract and post-surgical), retinitis pigmentosa, pars planitis, birdshot retinochoroidopathy, epiretinal membrane, cystic macular edema, parafoveal telengiectasis, tractional maculopathies, vitreomacular traction syndromes, retinal detachment, neuroretinitis, idiopathic macular edema, retinitis, dry eye (keratoconjunctivitis Sicca), vernal keratoconjunctivitis, atopic keratoconjunctivitis, uveitis (such as anterior uveitis, pan uveitis, posterior uveitis, uveitis-associated macular edema), scleritis, diabetic retinopathy, diabetic macula edema, age-related macular dystrophy, hepatitis, pancreatitis, primary biliary cirrhosis, sclerosing cholangitis, Addison's disease, hypophysitis, thyroiditis, type I diabetes, type II diabetes, giant cell arteritis, nephritis including lupus nephritis, vasculitis with organ involvement such as glomerulonephritis, vasculitis including giant cell arteritis, Wegener's granulomatosis, Polyarteritis nodosa, Behcet's disease, Kawasaki disease, Takayasu's Arteritis, pyoderma gangrenosum, vasculitis with organ involvement and acute rejection of transplanted organs.

In one embodiment the acute or chronic autoimmune and/or inflammatory condition is a disorder of lipid metabolism via the regulation of APO-A1 such as hypercholesterolemia, atherosclerosis and Alzheimer's disease.

In another embodiment the acute or chronic autoimmune and/or inflammatory condition is a respiratory disorder such as asthma or chronic obstructive airways disease.

In another embodiment the acute or chronic autoimmune and/or inflammatory condition is a systemic inflammatory disorder such as rheumatoid arthritis, osteoarthritis, acute gout, psoriasis, systemic lupus erythematosus, multiple sclerosis or inflammatory bowel disease (Crohn's disease and Ulcerative colitis). In a particular embodiment the acute or chronic autoimmune and/or inflammatory condition is rheumatoid arthritis, in particular refractory (treatment resistant) rheumatoid arthritis.

In another embodiment the acute or chronic autoimmune and/or inflammatory condition is multiple sclerosis.

In a further embodiment the acute or chronic autoimmune and/or inflammatory condition is Type I diabetes.

Bromodomain inhibitors may be useful in the treatment of diseases or conditions which involve inflammatory responses to infections with bacteria, viruses, fungi, parasites or their toxins, such as sepsis, acute sepsis, sepsis syndrome, septic shock, endotoxaemia, systemic inflammatory response syndrome (SIRS), multi-organ dysfunction syndrome, toxic shock syndrome, acute lung injury, ARDS (adult respiratory distress syndrome), acute renal failure, fulminant hepatitis, burns, acute pancreatitis, post-surgical syndromes, sarcoidosis, Herxheimer reactions, encephalitis, myelitis, meningitis, malaria and SIRS associated with viral infections such as influenza, herpes zoster, herpes simplex and coronavirus. In one embodiment the disease or condition which involves an inflammatory response to an infection with bacteria, a virus, fungi, a parasite or their toxins is acute sepsis.

Bromodomain inhibitors may be useful in the treatment of conditions associated with ischaemia-reperfusion injury such as myocardial infarction, cerebro-vascular ischaemia (stroke), acute coronary syndromes, renal reperfusion injury, organ transplantation, coronary artery bypass grafting, cardio-pulmonary bypass procedures, pulmonary, renal, hepatic, gastro-intestinal or peripheral limb embolism.

Bromodomain inhibitors may be useful in the treatment of cardiovascular diseases such as coronary artery diseases (for example, angina and myocardial infarction), cerebro-vascular ischaemia (stroke), heart failure, pulmonary arterial hypertension (PAH), hypertensive heart disease, rheumatic heart disease, cardiomyopathy, atrial fibrillation, congenital heart disease, endocarditis, aortic aneurysms and peripheral artery disease.

In one embodiment the disease or condition for which a bromodomain inhibitor is indicated is pulmonary arterial hypertension (PAH).

Bromodomain inhibitors may be useful in the treatment of fibrotic conditions such as idiopathic pulmonary fibrosis, renal fibrosis, post-operative stricture, keloid scar formation, scleroderma (including morphea) and cardiac fibrosis. In one embodiment the disease or condition for which a bromodomain inhibitor is indicated is scleroderma (systemic sclerosis).

Bromodomain inhibitors may be useful in the treatment of viral infections such as herpes simplex infections and reactivations, cold sores, herpes zoster infections and reactivations, chickenpox, shingles, human papilloma virus (HPV), human immunodeficiency virus (HIV), cervical neoplasia, adenovirus infections, including acute respiratory disease, poxvirus infections such as cowpox and smallpox and African swine fever virus. In one embodiment the viral infection is a HPV infection of skin or cervical epithelia. In another embodiment the viral infection is a latent HIV infection.

Bromodomain inhibitors may be useful in the treatment of a wide variety of bone disorders such as osteoporosis and osteopenia.

Bromodomain inhibitors may be useful in the treatment of cancer, including hematological (such as leukaemia, lymphoma and multiple myeloma), epithelial including lung, breast and colon carcinomas, midline carcinomas, mesenchymal, hepatic, renal and neurological tumours.

Bromodomain inhibitors may be useful in the treatment of one or more cancers selected from brain cancer (gliomas), glioblastomas, Bannayan-Zonana syndrome, Cowden disease, Lhermitte-Duclos disease, breast cancer, inflammatory breast cancer, colorectal cancer, Wilm's tumor, Ewing's sarcoma, rhabdomyosarcoma, ependymoma, medulloblastoma, colon cancer, head and neck cancer, kidney cancer, lung cancer, liver cancer, melanoma, squamous cell carcinoma, ovarian cancer, pancreatic cancer, prostate cancer, sarcoma cancer, osteosarcoma, giant cell tumor of bone, thyroid cancer, lymphoblastic T-cell leukemia, chronic myelogenous leukemia, chronic lymphocytic leukemia, hairy-cell leukemia, acute lymphoblastic leukemia, acute myelogenous leukemia, chronic neutrophilic leukemia, acute lymphoblastic T-cell leukemia, plasmacytoma, immunoblastic large cell leukemia, mantle cell leukemia, multiple myeloma, megakaryoblastic leukemia, acute megakaryocytic leukemia, promyelocytic leukemia, mixed lineage leukaemia, erythroleukemia, malignant lymphoma, Hodgkins lymphoma, non-Hodgkins lymphoma, lymphoblastic T-cell lymphoma, Burkitt's lymphoma, follicular lymphoma, neuroblastoma, bladder cancer, urothelial cancer, vulval cancer, cervical cancer, endometrial cancer, renal cancer, mesothelioma, esophageal cancer, salivary gland cancer, hepatocellular cancer, gastric cancer, nasopharangeal cancer, buccal cancer, cancer of the mouth, GIST (gastrointestinal stromal tumor), NUT-midline carcinoma and testicular cancer.

In one embodiment the cancer is a leukaemia, for example a leukaemia selected from acute monocytic leukemia, acute myelogenous leukemia, chronic myelogenous leukemia, chronic lymphocytic leukemia and mixed lineage leukaemia (MLL). In another embodiment the cancer is NUT-midline carcinoma. In another embodiment the cancer is multiple myeloma. In another embodiment the cancer is a lung cancer such as small cell lung cancer (SCLC). In another embodiment the cancer is a neuroblastoma. In another embodiment the cancer is Burkitt's lymphoma. In another embodiment the cancer is cervical cancer. In another embodiment the cancer is esophageal cancer. In another embodiment the cancer is ovarian cancer. In another embodiment the cancer is breast cancer. In another embodiment the cancer is colorectal cancer.

In one embodiment the disease or condition for which a bromodomain inhibitor is indicated is selected from diseases associated with systemic inflammatory response syndrome, such as sepsis, burns, pancreatitis, major trauma, haemorrhage and ischaemia. In this embodiment the bromodomain inhibitor would be administered at the point of diagnosis to reduce the incidence of SIRS, the onset of shock, multiorgan dysfunction syndrome, which includes the onset of acute lung injury, ARDS, acute renal, hepatic, cardiac or gastro-intestinal injury and mortality. In another embodiment the bromodomain inhibitor would be administered prior to surgical or other procedures associated with a high risk of sepsis, haemorrhage, extensive tissue damage, SIRS or MODS (multiple organ dysfunction syndrome). In a particular embodiment the disease or condition for which a bromodomain inhibitor is indicated is sepsis, sepsis syndrome, septic shock and endotoxaemia. In another embodiment, the bromodomain inhibitor is indicated for the treatment of acute or chronic pancreatitis. In another embodiment the bromodomain is indicated for the treatment of burns.

As used herein the reference to the "treatment" of a particular disease or condition includes the prevention or prophylaxis of such a disease or condition.

The term "diseases or conditions for which a bromodomain inhibitor is indicated", is intended to include each of or all of the above diseases or conditions.

While it is possible that for use in therapy, a compound of formula (I)-(XVI) as well as pharmaceutically acceptable salts thereof may be administered as the raw chemical, it is common to present the active ingredient as a pharmaceutical composition.

In a further aspect the present invention provides for a pharmaceutical composition comprising a compound of formula (I)-(XVI) or a pharmaceutically acceptable salt thereof and one or more pharmaceutically acceptable carriers, diluents or excipients.

In one embodiment the present invention provides for a pharmaceutical composition comprising (2S,3R,4R)-1-acetyl-4-((5-cyanopyridin-2-yl)amino)-N-ethyl-2,3-dimethyl-1,2,3,4-tetrahydroquinoline-6-carboxamide or a pharmaceutically acceptable salt thereof and one or more pharmaceutically acceptable carriers, diluents or excipients.

In one embodiment the present invention provides for a pharmaceutical composition comprising (2S,3R,4R)-1-acetyl-4-((5-cyanopyridin-2-yl)amino)-2,3-dimethyl-1,2,3,4-tetrahydroquinoline-6-carboxamide or a pharmaceutically acceptable salt thereof and one or more pharmaceutically acceptable carriers, diluents or excipients.

In one embodiment the present invention provides for a pharmaceutical composition comprising (2S,3R,4R)-1-acetyl-4-((5-cyanopyridin-2-yl)amino)-2,3-dimethyl-N-(tetrahydro-2H-pyran-4-yl)-1,2,3,4-tetrahydroquinoline-6-carboxamide or a pharmaceutically acceptable salt thereof and one or more pharmaceutically acceptable carriers, diluents or excipients.

In one embodiment the present invention provides for a pharmaceutical composition comprising (2S,3R,4R)-1-acetyl-4-((5-cyanopyridin-2-yl)amino)-N—((R)-2-hydroxypropyl)-2,3-dimethyl-1,2,3,4-tetrahydroquinoline-6-carboxamide or a pharmaceutically acceptable salt thereof and one or more pharmaceutically acceptable carriers, diluents or excipients.

In one embodiment the present invention provides for a pharmaceutical composition comprising (2S,3R,4R)-1-acetyl-4-((5-cyanopyridin-2-yl)amino)-N—((S)-2-hydroxypropyl)-2,3-dimethyl-1,2,3,4-tetrahydroquinoline-6-carboxamide or a pharmaceutically acceptable salt thereof and one or more pharmaceutically acceptable carriers, diluents or excipients.

In one embodiment the present invention provides for a pharmaceutical composition comprising (2S,3R,4R)-1-acetyl-4-((5-chloropyrimidin-2-yl)amino)-N-ethyl-2,3-dimethyl-1,2,3,4-tetrahydroquinoline-6-carboxamide or a pharmaceutically acceptable salt thereof and one or more pharmaceutically acceptable carriers, diluents or excipients.

In one embodiment the present invention provides for a pharmaceutical composition comprising (2S,3R,4R)-1-acetyl-4-((5-chloropyrimidin-2-yl)amino)-2,3-dimethyl-1,2,3,4-tetrahydroquinoline-6-carboxamide or a pharmaceutically acceptable salt thereof and one or more pharmaceutically acceptable carriers, diluents or excipients.

In one embodiment the present invention provides for a pharmaceutical composition comprising (2S,3R,4R)-1-acetyl-4-((5-chloropyrimidin-2-yl)amino)-2,3-dimethyl-N-(tetrahydro-2H-pyran-4-yl)-1,2,3,4-tetrahydroquinoline-6-carboxamide or a pharmaceutically acceptable salt thereof and one or more pharmaceutically acceptable carriers, diluents or excipients.

In one embodiment the present invention provides for a pharmaceutical composition comprising (2S,3R,4R)-1-acetyl-4-((5-chloropyrimidin-2-yl)amino)-N—((S)-2-hydroxypropyl)-2,3-dimethyl-1,2,3,4-tetrahydroquinoline-6-carboxamide or a pharmaceutically acceptable salt thereof and one or more pharmaceutically acceptable carriers, diluents or excipients.

In one embodiment the present invention provides for a pharmaceutical composition comprising (2S,3R,4R)-1-acetyl-4-((5-chloropyrimidin-2-yl)amino)-N—((R)-2-hydroxypropyl)-2,3-dimethyl-1,2,3,4-tetrahydroquinoline-6-carboxamide or a pharmaceutically acceptable salt thereof and one or more pharmaceutically acceptable carriers, diluents or excipients.

In one embodiment the present invention provides for a pharmaceutical composition comprising (2S,3R,4R)-1-acetyl-4-((5-cyanopyrazin-2-yl)amino)-2,3-dimethyl-1,2,3,4-tetrahydroquinoline-6-carboxamide or a pharmaceutically acceptable salt thereof and one or more pharmaceutically acceptable carriers, diluents or excipients.

In one embodiment the present invention provides for a pharmaceutical composition comprising (2S,3R,4R)-1-acetyl-4-((5-cyanopyrazin-2-yl)amino)-N-ethyl-2,3-dimethyl-1,2,3,4-tetrahydroquinoline-6-carboxamide or a pharmaceutically acceptable salt thereof and one or more pharmaceutically acceptable carriers, diluents or excipients.

In one embodiment the present invention provides for a pharmaceutical composition comprising (2S,3R,4R)-1-acetyl-N-ethyl-4-((5-fluoropyridin-2-yl)amino)-2,3-dimethyl-1,2,3,4-tetrahydroquinoline-6-carboxamide or a pharmaceutically acceptable salt thereof and one or more pharmaceutically acceptable carriers, diluents or excipients.

In one embodiment the present invention provides for a pharmaceutical composition comprising (2S,4R)-1-acetyl-4-((5-chloropyrimidin-2-yl)amino)-2-methyl-1,2,3,4-tetrahydroquinoline-6-carboxamide or a pharmaceutically acceptable salt thereof and one or more pharmaceutically acceptable carriers, diluents or excipients.

In one embodiment the present invention provides for a pharmaceutical composition comprising (2S,4R)-1-acetyl-4-((5-chloropyrimidin-2-yl)amino)-N-ethyl-2-methyl-1,2,3,4-tetrahydroquinoline-6-carboxamide or a pharmaceutically acceptable salt thereof and one or more pharmaceutically acceptable carriers, diluents or excipients.

In one embodiment the present invention provides for a pharmaceutical composition comprising (2S,4R)-1-acetyl-4-((5-cyanopyridin-2-yl)amino)-N-ethyl-2-methyl-1,2,3,4-tetrahydroquinoline-6-carboxamide or a pharmaceutically acceptable salt thereof and one or more pharmaceutically acceptable carriers, diluents or excipients.

The carrier(s), diluent(s) or excipient(s) must be pharmaceutically acceptable in the sense of being compatible with the other ingredients of the composition and not deleterious to the recipient thereof. In accordance with another aspect of the invention there is also provided a process for the preparation of a pharmaceutical composition including admixing a compound of formula (I)-(XVI), or a pharmaceutically acceptable salt thereof, with one or more pharmaceutically acceptable carriers, diluents or excipients. The pharmaceutical composition can be used in the treatment of any of the conditions described herein.

Since the compounds of formulae (I)-(XVI) are intended for use in pharmaceutical compositions it will be readily understood that they are each preferably provided in substantially pure form, for example, at least 85% pure, especially at least 98% pure (% in a weight for weight basis).

Pharmaceutical compositions may be presented in unit dose forms containing a predetermined amount of active ingredient per unit dose. Preferred unit dosage compositions are those containing a daily dose or sub-dose, or an appropriate fraction thereof, of an active ingredient. Such unit doses may therefore be administered more than once a day.

Pharmaceutical compositions may be adapted for administration by any appropriate route, for example by the oral (including buccal or sublingual), rectal, inhaled, intranasal, topical (including buccal, sublingual or transdermal), ocular (including topical, intraocular, subconjunctival, episcleral, sub-Tenon), vaginal or parenteral (including subcutaneous, intramuscular, intravenous or intradermal) route. Such compositions may be prepared by any method known in the art of pharmacy, for example by bringing into association the active ingredient with the carrier(s) or excipient(s).

In one embodiment the pharmaceutical composition is adapted for parenteral administration, particularly intravenous administration.

In one embodiment the pharmaceutical composition is adapted for oral administration.

In one embodiment the pharmaceutical composition is adapted for topical administration.

Pharmaceutical compositions adapted for parenteral administration include aqueous and non-aqueous sterile injection solutions which may contain anti-oxidants, buffers, bacteriostats and solutes which render the composition isotonic with the blood of the intended recipient; and aqueous and non-aqueous sterile suspensions which may include suspending agents and thickening agents. The compositions may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

Pharmaceutical compositions adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert carrier such as ethanol, glycerol, water and the like. Powders suitable for incorporating into tablets or capsules may be prepared by reducing the compound to a suitable fine size (e.g. by micronisation) and mixing with a similarly prepared pharmaceutical carrier such as an edible carbohydrate, for example, starch or mannitol. Flavoring, preservative, dispersing and coloring agent can also be present.

Capsules may be made by preparing a powder mixture, as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, glidants, lubricants, sweetening agents, flavours, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of formula (I) and pharmaceutically acceptable salts thereof can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Compositions for oral administration may be designed to provide a modified release profile so as to sustain or otherwise control the release of the therapeutically active agent.

Where appropriate, dosage unit compositions for oral administration can be microencapsulated. The composition may be prepared to prolong or sustain the release as for example by coating or embedding particulate material in polymers, wax or the like.

Compositions can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Pharmaceutical compositions adapted for topical administration may be formulated as ointments, creams, suspensions, emulsions, lotions, powders, solutions, pastes, gels, foams, sprays, aerosols or oils. Such pharmaceutical compositions may include conventional additives which include, but are not limited to, preservatives, solvents to assist drug penetration, co-solvents, emollients, propellants, viscosity modifying agents (gelling agents), surfactants and carriers. In one embodiment there is provided a pharmaceutical composition adapted for topical administration which comprises between 0.01-10%, or between 0.01-1% of a compound of formula (I)-(XVI), or a pharmaceutically acceptable salt thereof, by weight of the composition.

For treatments of the eye or other external tissues, for example mouth and skin, the compositions are preferably applied as a topical ointment, cream, gel, spray or foam. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical compositions adapted for topical administrations to the eye include eye drops wherein the active ingredient is dissolved or suspended in a suitable carrier, especially an aqueous solvent. Compositions to be administered to the eye will have ophthalmically compatible pH and osmolality. One or more ophthalmically acceptable pH adjusting agents and/or buffering agents can be included in a composition of the invention, including acids such as acetic, boric, citric, lactic, phosphoric and hydrochloric acids; bases such as sodium hydroxide, sodium phosphate, sodium borate, sodium citrate, sodium acetate, and sodium lactate; and buffers such as citrate/dextrose, sodium bicarbonate and ammonium chloride. Such acids, bases, and buffers can be included in an amount required to maintain pH of the composition in an ophthalmically acceptable range. One or more ophthalmically acceptable salts can be included in the composition in an amount sufficient to bring osmolality of the composition into an ophthalmically acceptable range. Such salts include those having sodium, potassium or ammonium cations and chloride, citrate, ascorbate, borate, phosphate, bicarbonate, sulfate, thiosulfate or bisulfite anions.

The ocular delivery device may be designed for the controlled release of one or more therapeutic agents with multiple defined release rates and sustained dose kinetics and permeability. Controlled release may be obtained through the design of polymeric matrices incorporating different choices and properties of biodegradable/bioerodable polymers (e.g. poly(ethylene vinyl) acetate (EVA), superhydrolyzed PVA), hydroxyalkyl cellulose (HPC), methylcellulose (MC), hydroxypropyl methyl cellulose (HPMC), polycaprolactone, poly(glycolic) acid, poly(lactic) acid, polyanhydride, of polymer molecular weights, polymer crystallinity, copolymer ratios, processing conditions, surface finish, geometry, excipient addition and polymeric coatings that will enhance drug diffusion, erosion, dissolution and osmosis.

Pharmaceutical compositions for ocular delivery also include in situ gellable aqueous composition. Such a composition comprises a gelling agent in a concentration effective to promote gelling upon contact with the eye or with lacrimal fluid. Suitable gelling agents include but are not limited to thermosetting polymers. The term "in situ gellable" as used herein is includes not only liquids of low viscosity that form gels upon contact with the eye or with lacrimal fluid, but also includes more viscous liquids such as semi-fluid and thixotropic gels that exhibit substantially increased viscosity or gel stiffness upon administration to the eye. See, for example, Ludwig (2005) *Adv. Drug Deliv. Rev.* 3; 57:1595-639, herein incorporated by reference for purposes of its teachings of examples of polymers for use in ocular drug delivery.

Dosage forms for nasal or inhaled administration may conveniently be formulated as aerosols, solutions, suspensions, gels or dry powders.

For compositions suitable and/or adapted for inhaled administration, it is preferred that a compound of formula (I)-(XVI) or a pharmaceutically acceptable salt thereof, is in a particle-size-reduced form e.g. obtained by micronisation. The preferable particle size of the size-reduced (e.g. micronised) compound or salt is defined by a D50 value of about 0.5 to about 10 microns (for example as measured using laser diffraction).

Aerosol formulations, e.g. for inhaled administration, can comprise a solution or fine suspension of the active substance in a pharmaceutically acceptable aqueous or non-aqueous solvent. Aerosol formulations can be presented in single or multidose quantities in sterile form in a sealed container, which can take the form of a cartridge or refill for use with an atomising device or inhaler. Alternatively the sealed container may be a unitary dispensing device such as a single dose nasal inhaler or an aerosol dispenser fitted with a metering valve (metered dose inhaler) which is intended for disposal once the contents of the container have been exhausted.

Where the dosage form comprises an aerosol dispenser, it preferably contains a suitable propellant under pressure such as compressed air, carbon dioxide or an organic propellant such as a hydrofluorocarbon (HFC). Suitable HFC propellants include 1,1,1,2,3,3,3-heptafluoropropane and 1,1,1,2-tetrafluoroethane. The aerosol dosage forms can also take the form of a pump-atomiser. The pressurised aerosol may contain a solution or a suspension of the active compound. This may require the incorporation of additional excipients e.g. co-solvents and/or surfactants to improve the dispersion characteristics and homogeneity of suspension formulations. Solution formulations may also require the addition of co-solvents such as ethanol.

For pharmaceutical compositions suitable and/or adapted for inhaled administration, the pharmaceutical composition may be a dry powder inhalable composition. Such a composition can comprise a powder base such as lactose, glucose, trehalose, mannitol or starch, the compounds of formulae (I)-(XVI) or a pharmaceutically acceptable salt thereof (preferably in particle-size-reduced form, e.g. in micronised form), and optionally a performance modifier such as L-leucine or another amino acid and/or metal salt of stearic acid such as magnesium or calcium stearate. Preferably, the dry powder inhalable composition comprises a dry powder blend of lactose e.g. lactose monohydrate and the compound of formula (I)-(XVI) or salt thereof. Such compositions can be administered to the patient using a suitable device such as the DISKUS® device, marketed by GlaxoSmithKline which is for example described in GB 2242134 A.

The compounds of formulae (I)-(XVI) and pharmaceutically acceptable salts thereof may be formulated as a fluid formulation for delivery from a fluid dispenser, for example a fluid dispenser having a dispensing nozzle or dispensing orifice through which a metered dose of the fluid formulation is dispensed upon the application of a user-applied force to a pump mechanism of the fluid dispenser. Such fluid dispensers are generally provided with a reservoir of multiple metered doses of the fluid formulation, the doses being dispensable upon sequential pump actuations. The dispensing nozzle or orifice may be configured for insertion into the nostrils of the user for spray dispensing of the fluid formulation into the nasal cavity. A fluid dispenser of the aforementioned type is described and illustrated in WO-A-2005/044354.

A therapeutically effective amount of a compound of formula (I)-(XVI) or a pharmaceutically acceptable salt thereof, will depend upon a number of factors including, for example, the age and weight of the subject, the precise condition requiring treatment and its severity, the nature of the formulation, and the route of administration, and will ultimately be at the discretion of the attendant physician or veterinarian. In the pharmaceutical composition, each dosage unit for oral or parenteral administration preferably contains from 0.01 to 3000 mg, more preferably 0.5 to 1000 mg, of a compound of formula (I)-(XVI) or a pharmaceutically acceptable salt thereof, calculated as the free base. Each dosage unit for nasal or inhaled administration preferably contains from 0.001 to 50 mg, more preferably 0.01 to 5 mg, of a compound of formulae (I)-(XVI) or a pharmaceutically acceptable salt thereof, calculated as the free base.

The pharmaceutically acceptable compounds of formulae (I)-(XVI) and pharmaceutically acceptable salts thereof, can be administered in a daily dose (for an adult patient) of, for example, an oral or parenteral dose of 0.01 mg to 3000 mg per day, 0.5 to 1000 mg per day or 100 mg to 2500 mg per day, or a nasal or inhaled dose of 0.001 to 50 mg per day or 0.01 to 5 mg per day, of a compound of formula (I)-(XVI) or a pharmaceutically acceptable salt thereof, calculated as the free base. This amount may be given in a single dose per day or more usually in a number (such as two, three, four, five or six) of sub-doses per day such that the total daily dose is the same. An effective amount of a salt thereof, may be determined as a proportion of the effective amount of a compound of formula (I)-(XVI) per se.

The compounds of formulae (I)-(XVI) and pharmaceutically acceptable salts thereof may be employed alone or in combination with other therapeutic agents. Combination therapies according to the present invention thus comprise the administration of at least one compound of formula (I)-(XVI) or a pharmaceutically acceptable salt thereof, and the use of at least one other therapeutically active agent. The compound(s) of formulae (I)-(XVI) and pharmaceutically acceptable salts thereof, and the other therapeutically active agent(s) may be administered together in a single pharmaceutical composition or separately and, when administered separately this may occur simultaneously or sequentially in any order. The amounts of the compound(s) of formulae (I)-(XVI) and pharmaceutically acceptable salts thereof, and the other therapeutically active agent(s) and the relative timings of administration will be selected in order to achieve the desired combined therapeutic effect.

Thus in a further aspect, there is provided a combination product comprising a compound of formula (I)-(XVI) or a pharmaceutically acceptable salt thereof, together with one or more other therapeutically active agents.

In one embodiment, the compound of formula (I)-(XVI) or a pharmaceutically acceptable salt thereof, and pharmaceutical compositions comprising the same may be used in combination with or include one or more other therapeutic agents, for example selected from antibiotics, anti-virals, glucocorticosteroids, muscarinic antagonists beta-2 agonists and Vitamin D3 analogues. In a further embodiment a compound of formula (I)-(XVI) or a pharmaceutically acceptable salt thereof may be used in combination with a further therapeutic agent which is suitable for the treatment of cancer. Examples of such further therapeutic agents are described in Cancer Principles and Practice of Oncology by V. T. Devita and S. Hellman (editors), 6$^{th}$ edition (2001), Lippincott Williams & Wilkins Publishers. A person of ordinary skill in the art would be able to discern which combinations of agents would be useful based on the particular characteristics of the drugs and the cancer involved. Further therapeutic agents to be used in combination with the compound of formulae (I)-(XVI) or a pharmaceutically acceptable salt thereof include, but are not limited to, anti-microtubule agents (such as diterpenoids and vinca alkaloids); platinum coordination complexes; alkylating agents (such as nitrogen mustards, oxazaphosphorines, alkylsulphonates, nitrosoureas, and triazenes); antibiotic agents (such as anthracyclins, actinomycins and bleomycins); topoisomerase II inhibitors (such as epipodophyllotoxins); antimetabolites (such as purine and pyrimidine analogues and anti-folate compounds); topoisomerase I inhibitors (such as camptothecins; hormones and hormonal analogues); signal transduction pathway inhibitors (such as tyropsine receptor inhibitors); non-receptor tyrosine kinase angiogenesis inhibitors; immunotherapeutic agents; proapoptotic agents; epigenetic or transcriptional modulators (such as histone deacetylase inhibitors), cell cycle signaling inhibitors and inhibitors of hormone nuclear receptors.

It will be appreciated that when a compound of formula (I)-(XVI) or a pharmaceutically acceptable salt thereof, is administered in combination with other therapeutic agents normally administered by the inhaled, intravenous, oral or intranasal route, that the resultant pharmaceutical composition may be administered by the same routes. Alternatively the individual components of the composition may be administered by different routes.

One embodiment of the invention encompasses combinations comprising one or two other therapeutic agents.

It will be clear to a person skilled in the art that, where appropriate, the other therapeutic ingredient(s) may be used in the form of salts, for example as alkali metal or amine salts or as acid addition salts, or prodrugs, or as esters, for example lower alkyl esters, or as solvates, for example hydrates, to optimise the activity and/or stability and/or physical characteristics, such as solubility, of the therapeutic ingredient. It will be clear also that, where appropriate, the therapeutic ingredients may be used in optically pure form.

The combinations referred to above may conveniently be presented for use in the form of a pharmaceutical composition and thus pharmaceutical compositions comprising a combination as defined above together with a pharmaceutically acceptable diluent or carrier represent a further aspect of the invention.

The compounds of formulae (I)-(XVI) and pharmaceutically acceptable salts thereof, may be prepared by the methods described below or by similar methods. Thus the following Intermediates and Examples serve to illustrate their preparation but are not to be considered as limiting the scope of the invention in any way.

General Experimental

All temperatures referred to are in ° C.

The names of the following compounds have been obtained using the compound naming programme ChemDraw Ultra 12.0 or "ACD Name Pro 6.02".

Abbreviations

AcCl acetyl chloride
DCM dichloromethane
DIPEA diisopropylethylamine
DMAP 4-(dimethylamino)pyridine
DMF N,N-dimethylformamide
DMSO dimethylsulfoxide
Et$_2$O diethyl ether
EtOH ethanol
EtOAc ethyl acetate
h hour(s)
HATU O-(7-azabenzotriazol-1-yl)-N,N,N',N'-tetramethyluronium hexafluorophosphate
HCl hydrochloric acid
i-pent PEPPSI dichloro[1,3-bis(2,6-di-3-pentylphenyl)imidazol-2-ylidene](3-chloropyridyl) palladium(II)
LCMS liquid chromatography-mass spectrometry
LiOH lithium hydroxide
M molar (concentration)
MeOH methanol
MDAP mass directed autoprep
min minute(s)
N$_2$ nitrogen
NEt$_3$ triethylamine
Pd/C palladium on carbon
Pd$_2$(dba)$_3$ tris(dibenzylideneacetone)dipalladium
QPhos 1,2,3,4,5-pentaphenyl-1'-(di-tert-butylphosphino)ferrocene
Rt retention time
rt room temperature
s, sec second(s)
THF tetrahydrofuran
UPLC ultra performance liquid chromatography
LCMS Methodology
Formic Method
LC Conditions The UPLC analysis was conducted on an Acquity UPLC BEH C18 column (50 mm×2.1 mm, i.d. 1.7 µm packing diameter) at 40° C.

The solvents employed were:
A=0.1% v/v solution of formic acid in water
B=0.1% v/v solution of formic acid in acetonitrile
The gradient employed was:

| Time (min) | Flow rate (mL/min) | % A | % B |
| --- | --- | --- | --- |
| 0 | 1 | 97 | 3 |
| 1.5 | 1 | 0 | 100 |
| 1.9 | 1 | 0 | 100 |
| 2.0 | 1 | 97 | 3 |

The UV detection was a summed signal from wavelength of 210 nm to 350 nm.
MS Conditions
  MS: Waters ZQ
  Ionisation mode: Alternate-scan positive and negative electrospray
  Scan range: 100 to 1000 AMU
  Scan time: 0.27 sec
  Inter scan delay: 0.10 sec High pH Method
LC Conditions The UPLC analysis was conducted on an Acquity UPLC BEH C18 column (50 mm×2.1 mm, i.d. 1.7 μm packing diameter) at 40° C.

The solvents employed were:

A=10 mM ammonium hydrogen carbonate in water adjusted to pH10 with ammonia solution
B=acetonitrile The gradient employed was:

| Time (min) | Flow rate (mL/min) | % A | % B |
|---|---|---|---|
| 0 | 1 | 99 | 1 |
| 1.5 | 1 | 3 | 97 |
| 1.9 | 1 | 3 | 97 |
| 2.0 | 1 | 0 | 100 |

The UV detection was a summed signal from wavelength of 210 nm to 350 nm.
MS Conditions MS: Waters ZQ Ionisation mode: Alternate-scan positive and negative electrospray Scan range: 100 to 1000 AMU Scan time: 0.27 sec Inter scan delay: 0.10 sec

NMR

Spectra were run on a 400 MHz NMR machine at either 302 K or for VT spectra at 392-393 K.

Intermediate 1

(E)-benzyl prop-1-en-1-ylcarbamate

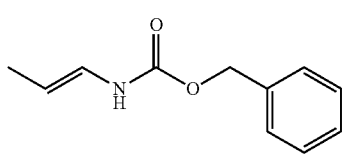

Diisopropyl azodicarboxylate (4.05 mL, 20.85 mmol) was added drop-wise over 5 min to a solution of triphenylphosphine (5.47 g, 20.85 mmol) in THF (125 mL) at −78° C. The mixture was stirred for min and then (2S,3R)-2-(((benzyloxy)carbonyl)amino)-3-hydroxybutanoic acid (4.8 g, 18.95 mmol) in THF (50 mL) was added drop-wise over 10 min still at −78° C. The solution was stirred for 1 h at −78° C. and allowed to warm to rt and stirred overnight. The solvent was then evaporated in vacuo and the residue was loaded onto a 100 g silica cartridge and purified by column chromatography using a gradient 0-30% of EtOAc/cyclohexane. Desired fractions were combined and evaporated in vacuo to give the product as a white solid (3.06 g). LCMS (2 min Formic): Rt=0.99 min, [MH]+ not observed.

Intermediate 2

(2S,3S,4R)-ethyl 4-(((benzyloxy)carbonyl)amino)-2,3-dimethyl-1,2,3,4-tetrahydroquinoline-6-carboxylate

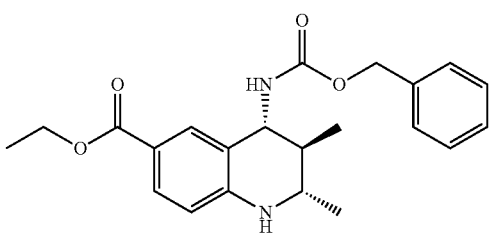 [SMILES: CCOC(=O)c1ccc2c(c1)[C@H](NC(=O)OCc1ccccc1)[C@@H](C)[C@H](C)N2]

Ethyl 4-aminobenzoate (15.6 g, 94 mmol) and acetaldehyde (8.00 mL, 142 mmol) were taken up in DCM (300 mL) and allowed to stir at rt for 1 h. The reaction was then cooled to 0° C. and treated with (E)-benzyl prop-1-en-1-ylcarbamate (for a preparation see Intermediate 1, 19.86 g, 104 mmol) and (11bS)-2,6-bis(4-chlorophenyl)-4-hydroxy-8,9,10,11,12,13,14,15-octahydrodinaphtho[2,1-d:1',2'-f][1,3,2]dioxaphosphepine 4-oxide (for a preparation see *JACS*, 2011, 133, 14804, 0.545 g, 0.944 mmol) the reaction was allowed to stir at 0° C. for 3 h, then the reaction mixture was added to a separating funnel. The mixture was diluted with DCM (300 mL), washed with saturated sodium bicarbonate solution (600 mL), giving a dense emulsion, from which the organic layer was separated after half an hour of waiting. The remaining aqueous emulsion was extracted with DCM (200 mL), then diluted with saturated brine (300 mL) and extracted again with DCM (200 mL). This mixture was allowed to stand overnight. The combined organics were dried and evaporated in vacuo to give a colourless solid. The solid was suspended in EtOAc (300 mL) and heated to reflux, giving a clear, colourless solution. This was diluted with cyclohexane until the mixture became turbid, then reheated to dissolve all solids, and allowed to cool to room temperature over 1 h. The suspension was filtered under vacuum and the solid product dried in the vacuum oven to give the product as a colourless solid (23.3 g). Analysis by chiral HPLC was undertaken using a 250×4.6 mm Chiralcel IC column eluting with 15% ethanol in heptane at a flow rate of 1 mL/min. Peak 1/minor enantiomer (0.2% by UV) eluted at 10.6 min, and Peak 2/major enantiomer (99.8% by UV) eluted at 15.4 min. This indicated the product had an ee of 99.6%. LCMS (2 min High pH): Rt=1.20 min, [MH]+=383.

Intermediate 3

(2S,3R,4R)-ethyl 1-acetyl-4-(((benzyloxy)carbonyl)amino)-2,3-dimethyl-1,2,3,4-tetrahydroquinoline-6-carboxylate

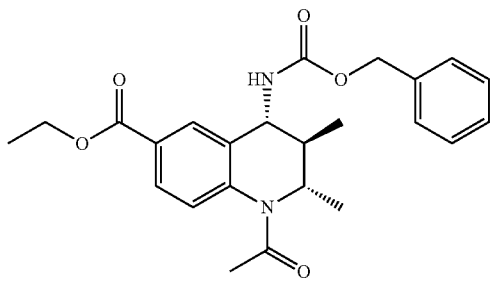 [SMILES: CCOC(=O)c1ccc2c(c1)[C@H](NC(=O)OCc1ccccc1)[C@@H](C)[C@H](C)N2C(C)=O]

A solution of (2S,3S,4R)-ethyl 4-(((benzyloxy)carbonyl)amino)-2,3-dimethyl-1,2,3,4-tetrahydroquinoline-6-carboxylate (for a preparation see Intermediate 2, 29.5 g, 77 mmol) and pyridine (18.72 mL, 231 mmol) in anhydrous DCM (800 mL) was cooled in an ice bath under nitrogen, then reacted with acetyl chloride (6.58 mL, 93 mmol) added dropwise over 10 min. The mixture was stirred at 0° C. for 1 h, then allowed to warm to room temperature and stirred for a further 3 h. The reaction mixture was transferred to a separating funnel and washed with 1 M HCl (500 mL), H$_2$O (500 mL) and saturated sodium bicarbonate solution (500 mL), dried and evaporated in vacuo to give the product (33.5 g). LCMS (2 min High pH): Rt=1.13 min, [MH]+=425

Intermediate 4

(2S,3R,4R)-ethyl 1-acetyl-4-amino-2,3-dimethyl-1,2,3,4-tetrahydroquinoline-6-carboxylate

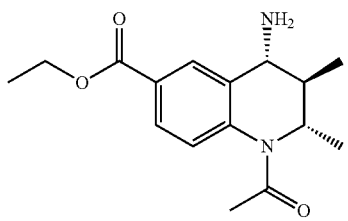 [SMILES: CCOC(=O)c1ccc2c(c1)[C@H](N)[C@@H](C)[C@H](C)N2C(C)=O]

A solution of (2S,3R,4R)-ethyl 1-acetyl-4-(((benzyloxy)carbonyl)amino)-2,3-dimethyl-1,2,3,4-tetrahydroquinoline-6-carboxylate (for a preparation see Intermediate 3, 7.5 g, 17.67 mmol) in ethanol (75 mL) was added to 5% Pd/C (wet) (1.43 g, 0.672 mmol) and stirred at room temperature under an atmosphere of hydrogen for 4.5 h. Further 5% Pd/C (wet) (1.43 g, 0.672 mmol) was added and the reaction was stirred under hydrogen for a further 16 h. Further 5% Pd/C (wet) (1.43 g, 0.672 mmol) was added and the reaction was stirred under hydrogen overnight. The reaction mixture was filtered through a 10 g Celite® cartridge washing through with extra EtOH. The filtrate was concentrated in vacuo and dried under vacuum overnight to leave the product as a viscous oil (4.5 g). LCMS (2 min Formic): Rt=0.49 min, [M]+=274 (loss of NH$_2$−).

Intermediate 5

(2S,3R,4R)-ethyl 1-acetyl-4-((5-cyanopyridin-2-yl)amino)-2,3-dimethyl-1,2,3,4-tetrahydroquinoline-6-carboxylate

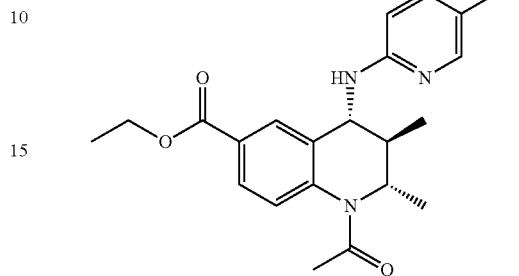

DIPEA (2.83 mL, 16.22 mmol) was added in a single portion to a stirred solution of (2S,3R,4R)-ethyl 1-acetyl-4-amino-2,3-dimethyl-1,2,3,4-tetrahydroquinoline-6-carboxylate (for a preparation see intermediate 4, 1.57 g, 5.41 mmol) and 6-fluoronicotinonitrile (1.320 g, 10.81 mmol) in DMSO (10 mL) at rt. The vial was sealed and then heated in a Biotage Initiator microwave using initial high absorption setting to 160° C. for 45 min. Upon cooling to rt, EtOAc (40 mL) and H$_2$O (40 mL) were added. The separated aqueous phase was extracted with EtOAc (2×40 mL). The combined organic phase was passed through a hydrophobic frit and evaporated under reduced pressure to give a brown oil. The oil was loaded in DCM and purified by column chromatography (100 g silica) using a gradient of 0-60% EtOAc/cyclohexane. The appropriate fractions were combined and evaporated under vacuum to give the product as a white foam (1.95 g). LCMS (2 min Formic): Rt=1.06 min, [MH]+=393.

Intermediate 6

(2S,3R,4R)-1-acetyl-4-((5-cyanopyridin-2-yl)amino)-2,3-dimethyl-1,2,3,4-tetrahydroquinoline-6-carboxylic acid

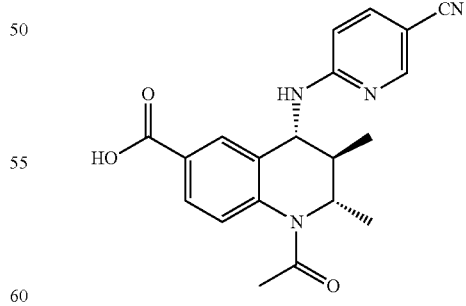

Lithium hydroxide (14.91 mL, 1 M in H$_2$O, 10.98 mmol) was added in a single portion to a stirred solution of (2S,3R,4R)-ethyl 1-acetyl-4-((5-cyanopyridin-2-yl)amino)-2,3-dimethyl-1,2,3,4-tetrahydroquinoline-6-carboxylate (for a preparation see Intermediate 5, 1.95 g, 4.97 mmol) in MeOH (15 mL) and THF (15 mL) at rt. The resultant solution was stirred at rt for 30 min and then allowed to stand at rt for 72 h. 2 M HCl (7.5 mL) was added, followed by H₂O (20 mL) and EtOAc (40 mL). The separated aqueous phase was extracted with EtOAc (2×20 mL). The combined organic phase was passed through a hydrophobic frit and evaporated under reduced pressure to give the product as a pale yellow foam (1.75 g). LCMS (2 min Formic): Rt=0.85 min, [MH]⁺=365.

Intermediate 7

(2S,3R,4R)-ethyl 1-acetyl-4-((5-chloropyrimidin-2-yl)amino)-2,3-dimethyl-1,2,3,4-tetrahydroquinoline-6-carboxylate

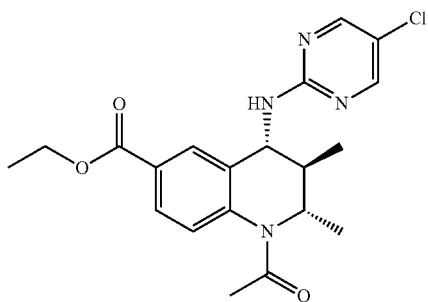

DIPEA (2.91 mL, 16.63 mmol) was added in a single portion to a stirred solution of (2S,3R,4R)-ethyl 1-acetyl-4-amino-2,3-dimethyl-1,2,3,4-tetrahydroquinoline-6-carboxylate (for a preparation see Intermediate 4, 1.61 g, 5.54 mmol) and 2,5-dichloropyrimidine (1.652 g, 11.09 mmol) in DMSO (10 mL) at rt. The vial was sealed and then heated in a Biotage Initiator microwave using initial high absorption setting to 160° C. for 90 min. Upon cooling to rt, EtOAc (40 mL) and H₂O (40 mL) were added. The separated aqueous phase was extracted with EtOAc (2×40 mL). The combined organic phase was passed through a hydrophobic frit and evaporated under reduced pressure to give a brown oil. The sample was loaded in DCM and purified by column chromatography (100 g silica) using a gradient of 0-50% EtOAc/cyclohexane. The appropriate fractions were combined and evaporated under vacuum to give the product as a pale yellow foam (1.475 g). LCMS (2 min Formic): Rt=1.15 min, [MH]⁺=403.

Intermediate 8

(2S,3R,4R)-1-acetyl-4-((5-chloropyrimidin-2-yl)amino)-2,3-dimethyl-1,2,3,4-tetrahydroquinoline-6-carboxylic acid

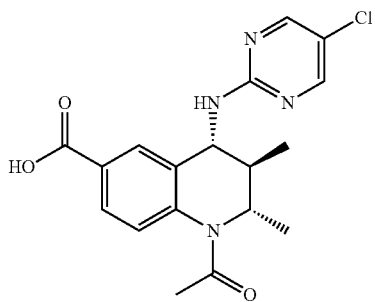

Lithium hydroxide (10.98 mL, 1 M in H₂O, 10.98 mmol) was added in a single portion to a stirred solution of (2S,3R,4R)-ethyl 1-acetyl-4-((5-chloropyrimidin-2-yl)amino)-2,3-dimethyl-1,2,3,4-tetrahydroquinoline-6-carboxylate (for a preparation see Intermediate 7, 1.475 g, 3.66 mmol) in MeOH (15 mL) and THF (15 mL) at rt. The resultant solution was stirred at rt for 30 min and then allowed to stand at rt for 72 h. 2 M HCl (5.5 mL) was added. H₂O (20 mL) and EtOAc (40 mL) were added, the separated aqueous phase was extracted with EtOAc (2×20 mL). The combined organic phase was passed through a hydrophobic frit and evaporated under reduced pressure to give the product as a pale yellow foam (1.36 g). LCMS (2 min Formic): Rt=0.92 min, [MH]⁺=375.

Intermediate 9

(2S,3R,4R)-ethyl 1-acetyl-4-((5-cyanopyrazin-2-yl)amino)-2,3-dimethyl-1,2,3,4-tetrahydroquinoline-6-carboxylate

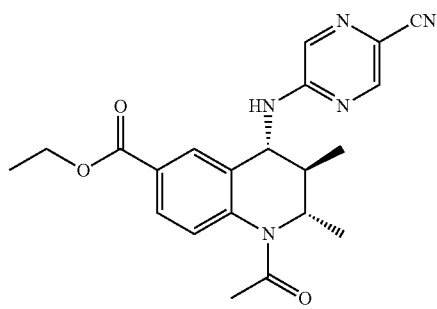 [SMILES: CCOC(=O)c1ccc2c(c1)[C@H](Nc1ccc(C#N)cn1)[C@@H](C)[C@H](C)N2C(C)=O]

To a microwave vial was added (2S,3R,4R)-ethyl 1-acetyl-4-amino-2,3-dimethyl-1,2,3,4-tetrahydroquinoline-6-carboxylate (for a preparation see Intermediate 4, 200 mg, 0.689 mmol) and 5-chloropyrazine-2-carbonitrile (192 mg, 1.378 mmol). DMSO (1 mL) was added, followed by DIPEA (0.361 mL, 2.066 mmol) and the microwave vial sealed and heated to 160° C. for 30 min in a microwave reactor. H₂O (20 mL) was added, followed by Et₂O (20 mL) and the layers separated. The aqueous layer was further extracted with Et₂O (2×20 mL) and the combined organics then back extracted with brine (2×20 mL). The combined organics were then dried (Na₂SO₄) and concentrated in vacuo to afford a brown oil. This was loaded in DCM and purified by column chromatography (25 g silica) using a gradient of 0-60% EtOAc/cyclohexane. The appropriate fractions were collected and concentrated in vacuo to afford the product as a brown oil (268 mg). LCMS (2 min Formic): Rt=1.01 min, [MH]⁺=394.

Intermediate 10

(2S,3R,4R)-1-acetyl-4-((5-cyanopyrazin-2-yl)amino)-2,3-dimethyl-1,2,3,4-tetrahydroquinoline-6-carboxylic acid

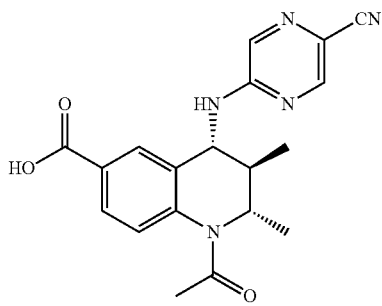 [SMILES: CC(=O)N1c2ccc(C(=O)O)cc2[C@H](Nc2cnc(C#N)cn2)[C@@H](C)[C@@H]1C]

(2S,3R,4R)-ethyl 1-acetyl-4-((5-cyanopyrazin-2-yl)amino)-2,3-dimethyl-1,2,3,4-tetrahydroquinoline-6-carboxylate (for a preparation see Intermediate 9, 268 mg, 0.681 mmol) was taken up in THF (1 mL) and H$_2$O (1 mL). Lithium hydroxide (48.9 mg, 2.044 mmol) was added and the reaction stirred for 19 h at rt. 2M HCl(aq) (1.022 mL, 2.044 mmol) was added and the reaction mixture was diluted with H$_2$O (20 mL) and extracted into 10% MeOH/DCM (3×20 mL). The combined organics were collected and concentrated in vacuo to afford the product as a yellow solid (72 mg). LCMS (2 min Formic): Rt=0.80 min, [MH]$^+$=366.

Intermediate 11

(2S,3R,4R)-ethyl 1-acetyl-4-((5-fluoropyridin-2-yl)amino)-2,3-dimethyl-1,2,3,4-tetrahydroquinoline-6-carboxylate

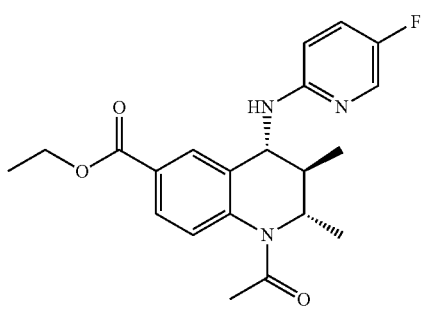 [SMILES: CCOC(=O)c1ccc2c(c1)[C@H](Nc1ccc(F)cn1)[C@@H](C)[C@H](C)N2C(C)=O]

To a flask was added (2S,3R,4R)-ethyl 1-acetyl-4-amino-2,3-dimethyl-1,2,3,4-tetrahydroquinoline-6-carboxylate (for a preparation see Intermediate 4, 150 mg, 0.517 mmol) and 2-bromo-5-fluoropyridine (182 mg, 1.033 mmol). 1,4-Dioxane (3.25 mL) was added, followed by cesium carbonate (370 mg, 1.137 mmol) and the flask had N$_2$ bubbled through it (5 min). Pd$_2$(dba)$_3$ (47.3 mg, 0.052 mmol) and QPhos (36.8 mg, 0.052 mmol) were added and the flask had further N$_2$ bubbled through it. The reaction was heated to 90° C. and allowed to stir for 3 h. Further Pd$_2$(dba)$_3$ (47.3 mg, 0.052 mmol) and QPhos (36.8 mg, 0.052 mmol) were added and the reaction allowed to stir at 90° C. overnight. Further 2-bromo-5-fluoropyridine (91 mg) was added and the reaction was heated at 110° C. for ~3 h. The reaction mixture was allowed to cool. The reaction mixture was diluted with EtOAc (20 mL) and filtered. The residues were washed with further EtOAc (20 mL) and the filtrate then concentrated in vacuo to afford a brown oil. This was loaded in DCM and purified by column chromatography (25 g silica) using a gradient of 0-60% EtOAc/cyclohexane. The appropriate fractions were collected and concentrated in vacuo to afford the product as an orange foam (37 mg). LCMS (2 min Formic): Rt=1.02 min, [MH]$^+$=386.

Intermediate 12

(2S,3R,4R)-1-acetyl-4-((5-fluoropyridin-2-yl)amino)-2,3-dimethyl-1,2,3,4-tetrahydroquinoline-6-carboxylic acid

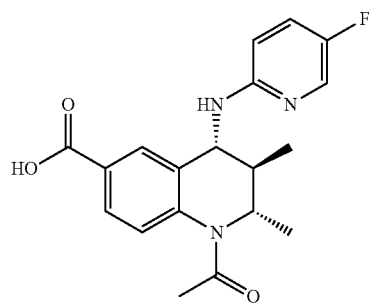 [SMILES: CC(=O)N1c2ccc(C(=O)O)cc2[C@H](Nc2ccc(F)cn2)[C@@H](C)[C@@H]1C]

(2S,3R,4R)-ethyl 1-acetyl-4-((5-fluoropyridin-2-yl)amino)-2,3-dimethyl-1,2,3,4-tetrahydroquinoline-6-carboxylate (for a preparation see Intermediate 11, 37 mg, 0.096 mmol) was taken up in THF (0.5 mL) and H$_2$O (0.5 mL). Lithium hydroxide (9.20 mg, 0.384 mmol) was added and the reaction stirred for 3 h at rtT. A further portion of LiOH (4 mg) was added and the reaction allowed to stir for 16 h at rt. 2M HCl(aq) (0.288 mL, 0.576 mmol) was added and the reaction mixture partitioned between 10% MeOH/DCM (20 mL) and H$_2$O (20 mL). The aqueous layer was washed with further 10% MeOH/DCM (2×20 mL) and the combined organics then dried and concentrated in vacuo to afford the product as a yellow oil (30 mg). LCMS (2 min Formic): Rt=0.66 min, [MH]$^+$=358.

Intermediate 13 tert-butyl ((2S,4R)-1-acetyl-6-cyano-2-methyl-1,2,3,4-tetrahydroquinolin-4-yl)carbamate

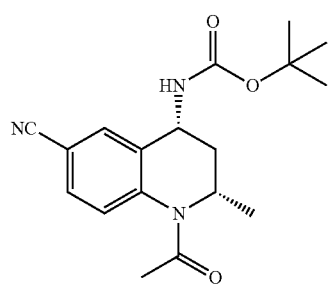 [SMILES: CC(=O)N1c2ccc(C#N)cc2[C@H](NC(=O)OC(C)(C)C)C[C@@H]1C]

A mixture of tert-butyl ((2S,4R)-1-acetyl-6-bromo-2-methyl-1,2,3,4-tetrahydroquinolin-4-yl)carbamate (for a preparation see Intermediate 29 in WO2012/143415A1, 2.0 g, 5.22 mmol) and zinc cyanide (766 mg, 6.52 mmol) in dry, degassed DMF (20 mL) was treated with tetrakis(triphenylphosphine)palladium(0) (301 mg, 5 mol %). The reaction mixture was stirred at 115° C. for 2 h. The reaction mixture was cooled to room temperature and filtered through Celite®. The solvent was evaporated from the filtrate. The residue was partitioned between EtOAc (100 mL) and $H_2O$ (50 mL). The organic phase was separated, washed with $H_2O$, brine, dried over $Na_2SO_4$ and evaporated. The residue was purified by column chromatography using a gradient of 25-50% EtOAc/cyclohexane to give the product (1.36 g) as a colourless solid. LCMS (2 min Formic): Rt=0.98 min, $[MH]^+=330$.

Intermediate 14

(2S,4R)-1-acetyl-4-amino-2-methyl-1,2,3,4-tetrahydroquinoline-6-carbonitrile hydrochloride

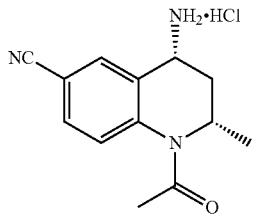

4 M hydrogen chloride in 1,4-dioxane (5 mL, 20 mmol) was added to a stirred solution of tert-butyl ((2S,4R)-1-acetyl-6-cyano-2-methyl-1,2,3,4-tetrahydroquinolin-4-yl)carbamate (for a preparation see Intermediate 13, 1.35 g, 4.1 mmol) in 1,4-dioxane (5 mL). The reaction mixture was stirred at rt for 24 h. $Et_2O$ (50 mL) was added and the mixture stirred for 20 min. The solvent was decanted. The residue was triturated with $Et_2O$ to give the product a colourless solid (0.98 g). LCMS (2 min High pH): Rt=0.65 min, $[M]^+=213$ (loss of $NH_2^-$).

Intermediate 15

(2S,4R)-1-acetyl-4-((5-chloropyrimidin-2-yl)amino)-2-methyl-1,2,3,4-tetrahydroquinoline-6-carbonitrile

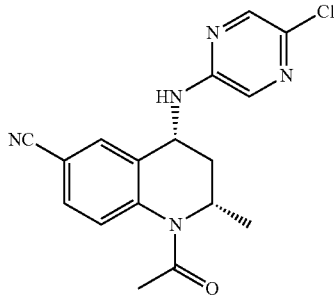 [SMILES: CC(=O)N1c2ccc(C#N)cc2[C@H](Nc2cnc(Cl)cn2)C[C@@H]1C]

DIPEA (0.493 mL, 2.82 mmol) was added in a single portion to a stirred solution of (2S,4R)-1-acetyl-4-amino-2-methyl-1,2,3,4-tetrahydroquinoline-6-carbonitrile, hydrochloride (for a preparation see Intermediate 14, 250 mg, 0.941 mmol) and 2,5-dichloropyrimidine (280 mg, 1.882 mmol) in DMSO (2 mL) at rt. The vial was sealed and then heated in a Biotage Initiator microwave using initial high absorption setting to 160° C. for 30 min. Upon cooling to rt, the vial was reheated in a Biotage Initiator microwave using initial high absorption setting to 160° C. for 30 min. Upon cooling to rt, EtOAc (10 mL) and $H_2O$ (10 mL) were added. The separated aqueous phase was extracted with EtOAc (2×10 mL). The combined organic phase was passed through a hydrophobic frit and evaporated under reduced pressure to give a brown oil. The oil was loaded in DCM and purified by column chromatography (25 g silica) using a gradient of 0-50% EtOAc/cyclohexane. The appropriate fractions were combined and evaporated under vacuum to give the product as a pale yellow oil (248 mg). LCMS (2 min Formic): Rt=0.94 min, $[MH]^+=342$.

Intermediate 16

(2S,4R)-butyl 1-acetyl-4-((isopropoxycarbonyl)amino)-2-methyl-1,2,3,4-tetrahydroquinoline-6-carboxylate

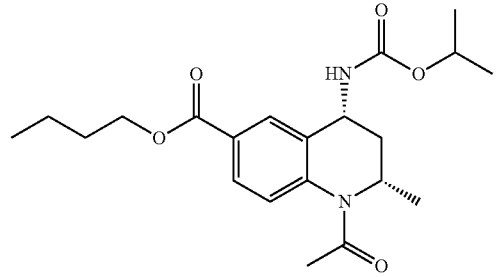 [SMILES: CCCCOC(=O)c1ccc2c(c1)[C@H](NC(=O)OC(C)C)C[C@H](C)N2C(C)=O]

Isopropyl ((2S,4R)-1-acetyl-6-bromo-2-methyl-1,2,3,4-tetrahydroquinolin-4-yl)carbamate (for a preparation see WO2012/143415A1, 5.7 g, 15.44 mmol) was taken up in 1,4-dioxane (20 mL) under $N_2$. Butan-1-ol (17.16 g, 232 mmol), DMAP (3.77 g, 30.9 mmol), DIPEA (5.50 mL, 31.5 mmol), trans-Bis(acetato)bis[o-(di-o-tolylphosphino)benzyl]dipalladium(II) (0.724 g, 0.772 mmol) and molybdenumhexacarbonyl (2.038 g, 7.72 mmol) were added and the mixture heated to 120° C. overnight. The reaction was cooled and filtered through Celite®. The filter cake was washed with EtOAc (100 mL). The filtrate was washed with $H_2O$ (100 mL) and the aqueous reextracted with EtOAc (100 mL). The combined organics were dried with $Na_2SO_4$, filtered and concentrated in vacuo to yield a brown oil. The oil was loaded in DCM and purified by column chromatography using a gradient of 5-50% EtOAc/cyclohexane. The appropriate fractions were concentrated in vacuo to give the product as a white solid (3.7282 g). LCMS (2 min High pH): Rt=1.20 min, $[MH]^+=391$.

Intermediate 17

(2S,4R)-butyl 1-acetyl-4-amino-2-methyl-1,2,3,4-tetrahydroquinoline-6-carboxylate

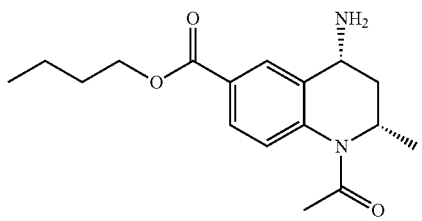 [SMILES: CCCCOC(=O)c1ccc2c(c1)[C@H](N)C[C@H](C)N2C(C)=O]

AlCl$_3$ (3.82 g, 28.7 mmol) was suspended in DCM (100 mL) under N$_2$ and cooled in an ice-bath and stirred. (2S,4R)-Butyl 1-acetyl-4-((isopropoxycarbonyl)amino)-2-methyl-1,2,3,4-tetrahydroquinoline-6-carboxylate (for a preparation see Intermediate 16, 2.9448 g, 7.54 mmol) was added and the mixture stirred for 30 min producing a clear solution. NEt$_3$ (12.61 mL, 90 mmol) in MeOH (13.33 mL) was slowly added producing a thick white precipitate. The reaction was stirred and allowed to warm to rt overnight. Further AlCl$_3$ (1.91 g) was added and stirring continued for a further 3 h. The reaction was cooled in an ice-bath and another portion of NEt$_3$ (6.3 mL) in MeOH (6.5 mL) was added. After stirring for a further 4 h, DCM (100 mL) and sat. NaHCO$_3$ (100 mL) were added to the the reaction mixture followed by Rochelle's salt (20 g) and stirring carried out for 30 min. H$_2$O (100 mL) was added and stirring continued for 30 min. DCM and H$_2$O (100 mL) were added and then separated. The aqueous was re-extracted with DCM (2×200 mL) and the combined organics filtered through Celite®, eluted through a hydrophobic frit and concentrated in vacuo to give a clear oil. The oil was loaded in DCM and purified by column chromatography using a gradient of 5-50% (3:1 EtOAc/EtOH)/cyclohexane. The appropriate fractions were concentrated in vacuo to give the product as a yellow oil (2.0818 g). LCMS (2 min High pH): Rt=0.98 min, [MH]$^+$=329.

Intermediate 18

(2S,4R)-butyl 1-acetyl-4-((5-chloropyrimidin-2-yl)amino)-2-methyl-1,2,3,4-tetrahydroquinoline-6-carboxylate

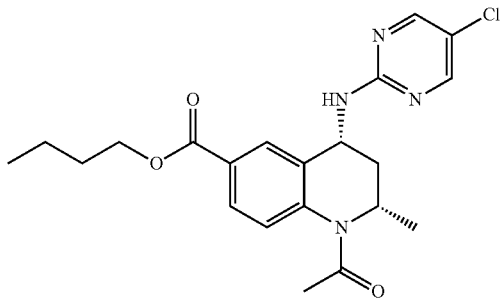 [SMILES: CCCCOC(=O)c1ccc2c(c1)[C@H](Nc1ncc(Cl)cn1)C[C@H](C)N2C(C)=O]

DIPEA (0.344 mL, 1.971 mmol) was added in a single portion to a stirred solution of (2S,4R)-butyl 1-acetyl-4-amino-2-methyl-1,2,3,4-tetrahydroquinoline-6-carboxylate (for a preparation see Intermediate 17, 200 mg, 0.657 mmol) and 2,5-dichloropyrimidine (196 mg, 1.314 mmol) in DMSO (2 mL) at rt. The vial was sealed and then heated in a Biotage Initiator microwave using initial high absorption setting to 160° C. for 40 min. Upon cooling to rt, EtOAc (10 mL) and H$_2$O (10 mL) were added. The separated aqueous phase was extracted with EtOAc (2×10 mL). The combined organic phase was passed through a hydrophobic frit and evaporated under reduced pressure to give a brown oil. The sample was loaded in DCM and purified by column chromatography (25 g, silica) using a gradient of 0-40% EtOAc/cyclohexane. The appropriate fractions were combined and evaporated under vacuum to give the product as a pale yellow oil (265 mg). LCMS (2 min Formic): Rt=1.23 min, [MH]$^+$=417.

Intermediate 19

(2S,4R)-1-acetyl-4-((5-chloropyrimidin-2-yl)amino)-2-methyl-1,2,3,4-tetrahydroquinoline-6-carboxylic acid

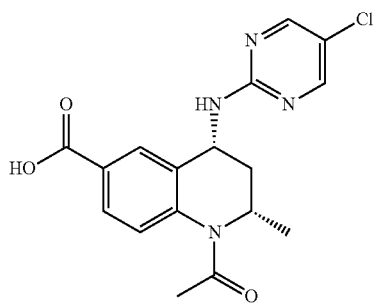 [SMILES: CC(=O)N1c2ccc(C(=O)O)cc2[C@H](Nc2ncc(Cl)cn2)C[C@@H]1C]

Lithium hydroxide (1.91 mL, 1 M in H$_2$O, 1.91 mmol) was added in a single portion to a stirred solution of (2S,4R)-butyl 1-acetyl-4-((5-chloropyrimidin-2-yl)amino)-2-methyl-1,2,3,4-tetrahydroquinoline-6-carboxylate (for a preparation see Intermediate 18, 265 mg, 0.636 mmol) in MeOH (2 mL) and THF (2 mL) at rt. The resultant solution was stirred at rt for 2 h and then 2 M HCl (1 mL) was added. H$_2$O (20 mL) and EtOAc (20 mL) were added, the separated aqueous phase was extracted with EtOAc (2×10 mL). The combined organic phase was passed through a hydrophobic frit and evaporated under reduced pressure to give the product as a yellow oil (212 mg). LCMS (2 min Formic): Rt=0.83 min, [MH]$^+$=361.

Intermediate 20

(2S,4R)-butyl 1-acetyl-4-amino-2-methyl-1,2,3,4-tetrahydroquinoline-6-carboxylate hydrochloride

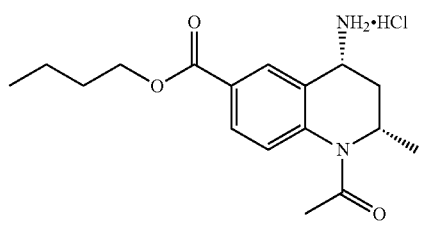

A solution of (2S,4R)-butyl 1-acetyl-4-amino-2-methyl-1,2,3,4-tetrahydroquinoline-6-carboxylate (for a preparation see Intermediate 17, 1.95 g, 6.41 mmol) in Et$_2$O (20 mL) was treated with 1.0 M HCl in Et$_2$O (3.0 mL). The solvent was evaporated to give the product as a pale yellow solid (1.8 g). LCMS (2 min Formic): Rt=0.64 min, [M]$^+$=288 (loss of NH$_2^-$).

Intermediate 21

(2S,4R)-butyl 1-acetyl-4-((5-cyanopyridin-2-yl)amino)-2-methyl-1,2,3,4-tetrahydroquinoline-6-carboxylate

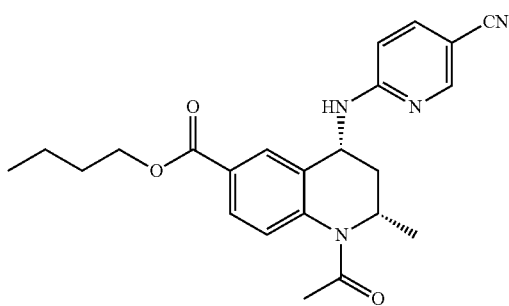 [SMILES: CCCCOC(=O)c1ccc2c(c1)[C@H](Nc1ccc(C#N)cn1)C[C@H](C)N2C(C)=O]

DIPEA (0.384 mL, 2.200 mmol) was added in a single portion to a stirred solution of (2S,4R)-butyl 1-acetyl-4-amino-2-methyl-1,2,3,4-tetrahydroquinoline-6-carboxylate, hydrochloride (for a preparation see Intermediate 20, 250 mg, 0.733 mmol) and 6-fluoronicotinonitrile (179 mg, 1.467 mmol) in DMSO (2 mL) at rt. The vial was sealed and then heated in a Biotage Initiator microwave using initial high absorption setting to 160° C. for 30 min. Upon cooling to rt, EtOAc (10 mL) and H$_2$O (10 mL) were added. The separated aqueous phase was extracted with EtOAc (2×10 mL). The combined organic phase was passed through a hydrophobic frit and evaporated under reduced pressure to give a brown oil. The sample was loaded in DCM and purified by column chromatography (25 g, silica) using a gradient of 0-40% EtOAc/cyclohexane. The appropriate fractions were combined and evaporated under vacuum to give the product as a pale yellow oil (285 mg). LCMS (2 min Formic): Rt=1.15 min, [MH]$^+$=407.

Intermediate 22

(2S,4R)-1-acetyl-4-((5-cyanopyridin-2-yl)amino)-2-methyl-1,2,3,4-tetrahydroquinoline-6-carboxylic acid

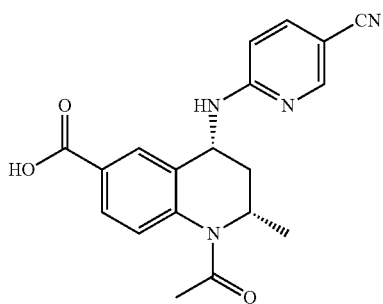 [SMILES: CC(=O)N1c2ccc(C(=O)O)cc2[C@H](Nc2ccc(C#N)cn2)C[C@@H]1C]

Lithium hydroxide (2.10 mL, 1 M in H$_2$O, 2.10 mmol) was added in a single portion to a stirred solution of (2S,4R)-butyl 1-acetyl-4-((5-cyanopyridin-2-yl)amino)-2-methyl-1,2,3,4-tetrahydroquinoline-6-carboxylate (for a preparation see Intermediate 21, 285 mg, 0.701 mmol) in MeOH (2 mL) and THF (2 mL) at rt. The resultant solution was stirred at rt for 2 h and then 2 M HCl (1 mL) was added. H$_2$O (20 mL) and EtOAc (20 mL) were added, the separated aqueous phase was extracted with EtOAc (2×10 mL). The combined organic phase was passed through a hydrophobic frit and evaporated under reduced pressure to give the product as a pale yellow foam (223 mg). LCMS (2 min Formic): Rt=0.78 min, [MH]$^+$=351.

Intermediate 23

(2S,3R,4R)-ethyl 1-acetyl-4-((5-chloropyridin-2-yl)amino)-2,3-dimethyl-1,2,3,4-tetrahydroquinoline-6-carboxylate

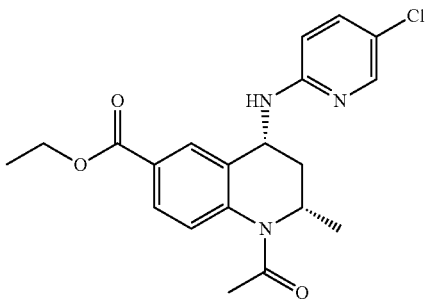 [SMILES: CCOC(=O)c1ccc2c(c1)[C@H](Nc1ccc(Cl)cn1)C[C@H](C)N2C(C)=O]

A mixture of (2S,3R,4R)-ethyl 1-acetyl-4-amino-2,3-dimethyl-1,2,3,4-tetrahydroquinoline-6-carboxylate (for a preparation see Intermediate 4, 295.0 mg, 1.016 mmol), 2-bromo-5-chloropyridine (217.2 mg, 1.129 mmol), i-pent PEPPSI (40.7 mg, 0.051 mmol) and cesium carbonate (654.4 mg, 2.008 mmol) in 1,4-dioxane (3 mL) was heated with stirring under N$_2$ at ≥100° C. for 22.5 h. After allowing to cool, the mixture was filtered through Celite, eluting with EtOAc (3×5 mL). The combined filtrate was concentrated under a stream of N$_2$ and the residue purified by MDAP. The required fractions were concentrated under a stream of N$_2$, combined and then evaporated to dryness in vacuo to give the product as a light brown gum, (46.8 mg). LCMS (2 min Formic): Rt=1.15 min, [MH]$^+$=402.

Intermediate 24

(2S,3R,4R)-1-acetyl-4-((5-chloropyridin-2-yl)amino)-2,3-dimethyl-1,2,3,4-tetrahydroquinoline-6-carboxylic acid

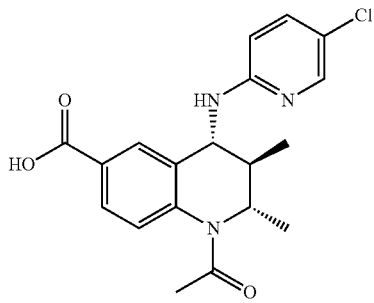 [SMILES: CC(=O)N1c2ccc(C(=O)O)cc2[C@H](Nc2ccc(Cl)cn2)[C@@H](C)[C@@H]1C]

(2S,3R,4R)-ethyl 1-acetyl-4-((5-chloropyridin-2-yl)amino)-2,3-dimethyl-1,2,3,4-tetrahydroquinoline-6-carboxylate (for a preparation see Intermediate 23, 67.7 mg, 0.168 mmol) was stirred in THF (0.5 mL) and H$_2$O (0.5 mL) under N$_2$. Lithium hydroxide (13.6 mg, 0.568 mmol) was added and the reaction stirred for at rt for 24 hr. After leaving to stand overnight, the mixture was acidified by the addition of 2 M HCl (3 mL) and was extracted with EtOAc (3×3 mL). The phases were separated and the organic phase was dried by passing it through a hydrophobic frit. The volatiles were evaporated from both phases under a stream of N$_2$, the residues were combined and purified by MDAP. The required fractions were concentrated under a stream of N$_2$, the residues combined and dried in vacuo to give the product as a cream solid (48 mg). LCMS (2 min Formic): Rt=0.89 min, [MH]$^+$=374.

Example 1

(2S,3R,4R)-1-acetyl-4-((5-cyanopyridin-2-yl)amino)-N-ethyl-2,3-dimethyl-1,2,3,4-tetrahydroquinoline-6-carboxamide

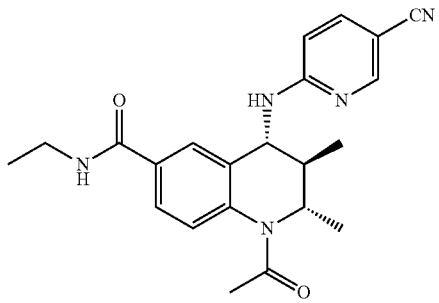

(2S,3R,4R)-1-acetyl-4-((5-cyanopyridin-2-yl)amino)-2,3-dimethyl-1,2,3,4-tetrahydroquinoline-6-carboxylic acid (for a preparation see Intermediate 6, 88 mg, 0.121 mmol) was taken up in DMF (1.4 mL) and HATU (50.5 mg, 0.133 mmol) followed by DIPEA (0.042 mL, 0.241 mmol) was added. The reaction mixture was allowed to stir for 5 min, then ethanamine (2 M in THF) (0.121 mL, 0.241 mmol) was added and the reaction allowed to stir at rt for ~1 h. The reaction mixture was added directly to a vial and the flask washed with 2 portions of MeOH/DMSO (1:1, 0.2 mL). The vial was purified directly by MDAP. The appropriate fractions were collected and concentrated in vacuo to afford the product as a cream solid (32 mg). LCMS (2 min Formic): Rt=0.82 min, [MH]$^+$=392.

Example 2

(2S,3R,4R)-1-acetyl-4-((5-cyanopyridin-2-yl)amino)-2,3-dimethyl-1,2,3,4-tetrahydroquinoline-6-carboxamide

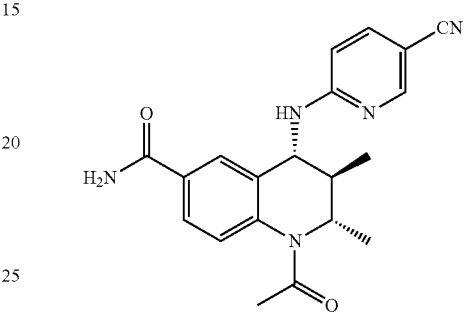

(2S,3R,4R)-1-acetyl-4-((5-cyanopyridin-2-yl)amino)-2,3-dimethyl-1,2,3,4-tetrahydroquinoline-6-carboxylic acid (for a preparation see intermediate 6, 88 mg, 0.121 mmol) was taken up in DMF (1.4 mL) and HATU (50.5 mg, 0.133 mmol) followed by DIPEA (0.042 mL, 0.241 mmol) was added. The reaction mixture was allowed to stir for 5 min, then ammonium chloride (12.92 mg, 0.241 mmol) was added and the reaction allowed to stir at rt for ~1 h. The reaction mixture was added directly to a vial and the flask washed with 2 portions of MeOH/DMSO (1:1, 0.2 mL). The vial was purified directly by MDAP. The appropriate fractions were collected and concentrated in vacuo to afford the product as a cream solid (28 mg). LCMS (2 min Formic): Rt=0.72 min, [MH]$^+$=364.

Example 3

(2S,3R,4R)-1-acetyl-4-((5-cyanopyridin-2-yl)amino)-2,3-dimethyl-N-(tetrahydro-2H-pyran-4-yl)-1,2,3,4-tetrahydroquinoline-6-carboxamide

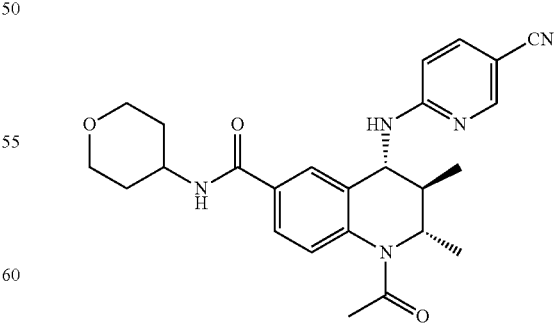

HATU (172 mg, 0.453 mmol) was added in a single portion to a stirred solution of (2S,3R,4R)-1-acetyl-4-((5-cyanopyridin-2-yl)amino)-2,3-dimethyl-1,2,3,4-tetrahydroquinoline-6-carboxylic acid (for a preparation see Intermediate 6, 150 mg, 0.412 mmol) and DIPEA (0.216 mL, 1.235 mmol) in DMF (2 mL) at rt under N₂. Following stirring at rt for 15 min, tetrahydro-2H-pyran-4-amine hydrochloride salt (113 mg, 0.823 mmol) was added in a single portion and the resultant solution was stirred at rt for 30 min. The DMF solution was then purified by MDAP. The appropriate fractions were combined and the solvent was evaporated under vacuum to give the product as a white solid (81 mg). LCMS (2 min Formic): Rt=0.82 min, [MH]⁺=448.

Example 4

(2S,3R,4R)-1-acetyl-4-((5-cyanopyridin-2-yl)amino)-N—((R)-2-hydroxypropyl)-2,3-dimethyl-1,2,3,4-tetrahydroquinoline-6-carboxamide

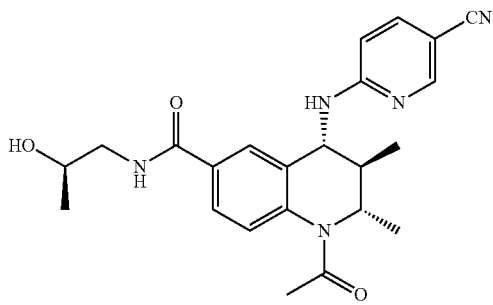 [SMILES: CC(=O)N1c2ccc(C(=O)NC[C@@H](C)O)cc2[C@H](Nc2ccc(C#N)cn2)[C@@H](C)[C@@H]1C]

HATU (172 mg, 0.453 mmol) was added in a single portion to a stirred solution of (2S,3R,4R)-1-acetyl-4-((5-cyanopyridin-2-yl)amino)-2,3-dimethyl-1,2,3,4-tetrahydroquinoline-6-carboxylic acid (for a preparation see Intermediate 6, 150 mg, 0.412 mmol) and DIPEA (0.216 mL, 1.235 mmol) in DMF (2 mL) at rt under N₂. Following stirring at rt for 15 min, (R)-1-aminopropan-2-ol (62 mg, 0.825 mmol) was added in a single portion. The resultant solution was stirred at rt for 30 min. The DMF solution was then purified by MDAP. The appropriate fractions were combined and the solvent was evaporated under vacuum to give the product as a white solid (119 mg). LCMS (2 min Formic): Rt=0.75 min, [MH]⁺=422.

Example 5

(2S,3R,4R)-1-acetyl-4-((5-cyanopyridin-2-yl)amino)-N—((S)-2-hydroxypropyl)-2,3-dimethyl-1,2,3,4-tetrahydroquinoline-6-carboxamide

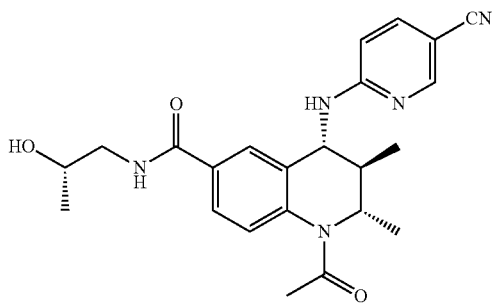 [SMILES: CC(=O)N1c2ccc(C(=O)NC[C@H](C)O)cc2[C@H](Nc2ccc(C#N)cn2)[C@@H](C)[C@@H]1C]

HATU (172 mg, 0.453 mmol) was added in a single portion to a stirred solution of (2S,3R,4R)-1-acetyl-4-((5-cyanopyridin-2-yl)amino)-2,3-dimethyl-1,2,3,4-tetrahydroquinoline-6-carboxylic acid (for a preparation see Intermediate 6, 150 mg, 0.412 mmol) and DIPEA (0.216 mL, 1.235 mmol) in DMF (2 mL) at rt under N₂. Following stirring at rt for 15 min, (S)-1-aminopropan-2-ol (0.065 mL, 0.823 mmol) was added in a single portion. The resultant solution was stirred at rt for 30 min. The DMF solution was then purified by MDAP. The appropriate fractions were combined and the solvent was evaporated under vacuum to give the product as a white solid (121 mg). LCMS (2 min Formic): Rt=0.75 min, [MH]⁺=422.

Example 6

((2S,3R,4R)-1-acetyl-4-((5-chloropyrimidin-2-yl)amino)-N-ethyl-2,3-dimethyl-1,2,3,4-tetrahydroquinoline-6-carboxamide

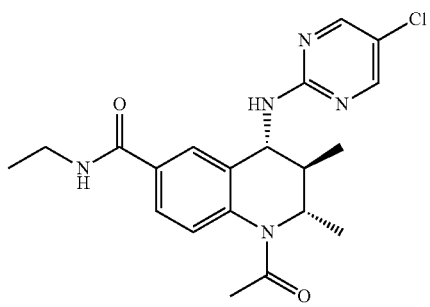 [SMILES: CCNC(=O)c1ccc2c(c1)[C@H](Nc1ncc(Cl)cn1)[C@@H](C)[C@H](C)N2C(C)=O]

A mixture of (2S,3R,4R)-1-acetyl-4-((5-chloropyrimidin-2-yl)amino)-2,3-dimethyl-1,2,3,4-tetrahydroquinoline-6-carboxylic acid (for a preparation see Intermediate 8, 96.6 mg, 0.258 mmol), ethylamine (0.5 mL, 2 M in THF, 1.000 mmol) and HATU (117.5 mg, 0.309 mmol) in DMF (1.5 mL) had a solution of (2S,3R,4R)-1-acetyl-4-((5-chloropyridin-2-yl)amino)-2,3-dimethyl-1,2,3,4-tetrahydroquinoline-6-carboxylic acid (for a preparation see Intermediate 24, 24.0 mg, 0.064 mmol) in DMF (0.5 mL). DIPEA (0.113 mL, 0.644 mmol) was added and the resulting mixture was stirred at rt for 2 h. The mixture was diluted with DMF to give a total volume of 3 mL and was then directly purified by MDAP. The required fractions were combined and the solvent was evaporated in vacuo to give the product as a white solid (58 mg). LCMS (2 min Formic): Rt=0.89 min, [MH]⁺=402.

Example 7

(2S,3R,4R)-1-acetyl-4-((5-chloropyrimidin-2-yl)amino)-2,3-dimethyl-1,2,3,4-tetrahydroquinoline-6-carboxamide

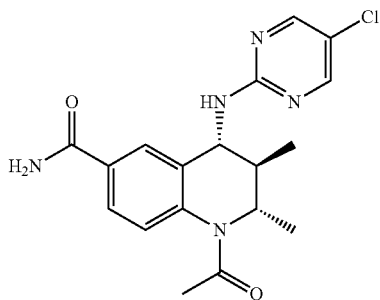 [SMILES: CC(=O)N1c2ccc(C(N)=O)cc2[C@H](Nc2ncc(Cl)cn2)[C@@H](C)[C@@H]1C]

A mixture of (2S,3R,4R)-1-acetyl-4-((5-chloropyrimidin-2-yl)amino)-2,3-dimethyl-1,2,3,4-tetrahydroquinoline-6-carboxylic acid (for a preparation see Intermediate 8, 97.1 mg, 0.259 mmol), ammonium chloride (71.4 mg, 1.335 mmol) and HATU (118.9 mg, 0.313 mmol) in DMF (1.5 mL) had a solution of (2S,3R,4R)-1-acetyl-4-((5-chloropyrimidin-2-yl)amino)-2,3-dimethyl-1,2,3,4-tetrahydroquinoline-6-carboxylic acid (for a preparation see Intermediate 24, 24.0 mg, 0.064 mmol) in DMF (0.5 mL) added. DIPEA (0.113 mL, 0.648 mmol) was added and the resulting mixture was stirred at rt for 2 h. The mixture was diluted with DMF to give a total volume of 3 mL and was then directly purified by MDAP. The required fractions were combined and the solvent was evaporated in vacuo to give the product as a white solid (72.9 mg). LCMS (2 min Formic): Rt=0.77 min, [MH]$^+$=374.

Example 8

(2S,3R,4R)-1-acetyl-4-((5-chloropyrimidin-2-yl)amino)-2,3-dimethyl-N-(tetrahydro-2H-pyran-4-yl)-1,2,3,4-tetrahydroquinoline-6-carboxamide

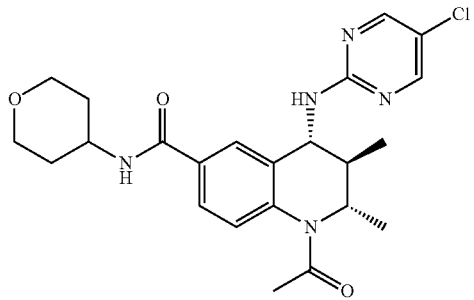 [SMILES: CC(=O)N1c2ccc(C(=O)NC3CCOCC3)cc2[C@H](Nc2ncc(Cl)cn2)[C@@H](C)[C@@H]1C]

HATU (167 mg, 0.440 mmol) was added in a single portion to a stirred solution of (2S,3R,4R)-1-acetyl-4-((5-chloropyrimidin-2-yl)amino)-2,3-dimethyl-1,2,3,4-tetrahydroquinoline-6-carboxylic acid (for a preparation see intermediate 8, 150 mg, 0.400 mmol) and DIPEA (0.210 mL, 1.201 mmol) in DMF (2 mL) at rt under N$_2$. Following stirring at rt for 15 min, tetrahydro-2H-pyran-4-amine, hydrochloride salt (110 mg, 0.800 mmol) was added in a single portion and the resultant solution was stirred at rt for 30 min. The DMF solution was then purified by MDAP. The appropriate fractions were combined and the solvent was evaporated under vacuum to give the product as a white solid (88 mg). LCMS (2 min Formic): Rt=0.89 min, [MH]$^+$=458.

Example 9

(2S,3R,4R)-1-acetyl-4-((5-chloropyrimidin-2-yl)amino)-N—((S)-2-hydroxypropyl)-2,3-dimethyl-1,2,3,4-tetrahydroquinoline-6-carboxamide

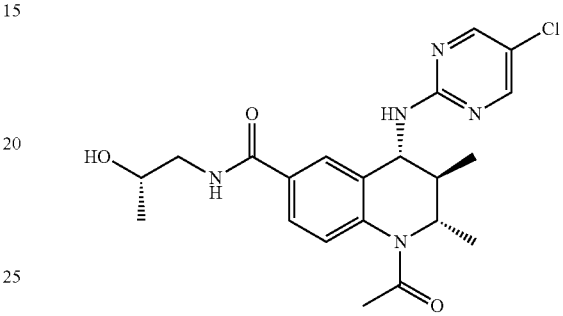

HATU (167 mg, 0.440 mmol) was added in a single portion to a stirred solution of (2S,3R,4R)-1-acetyl-4-((5-chloropyrimidin-2-yl)amino)-2,3-dimethyl-1,2,3,4-tetrahydroquinoline-6-carboxylic acid (for a preparation see Intermediate 8, 150 mg, 0.400 mmol) and DIPEA (0.210 mL, 1.201 mmol) in DMF (2 mL) at rt under N$_2$. Following stirring at rt for 15 min, (S)-1-aminopropan-2-ol (0.063 mL, 0.800 mmol) was added in a single portion. The resultant solution was stirred at rt for 30 min. The DMF solution was then purified by MDAP. The appropriate fractions were combined and the solvent was evaporated under vacuum to give the product as a white solid (120 mg). LCMS (2 min Formic): Rt=0.82 min, [MH]$^+$=432.

Example 10

(2S,3R,4R)-1-acetyl-4-((5-chloropyrimidin-2-yl)amino)-N—((R)-2-hydroxypropyl)-2,3-dimethyl-1,2,3,4-tetrahydroquinoline-6-carboxamide

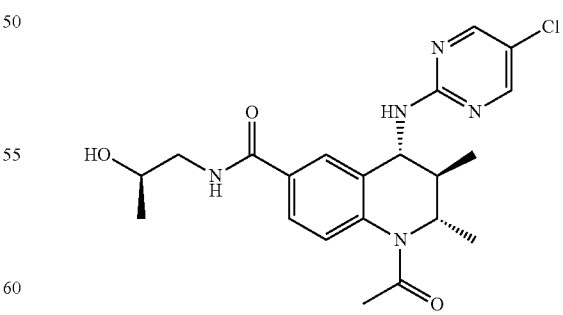

HATU (167 mg, 0.440 mmol) was added in a single portion to a stirred solution of (2S,3R,4R)-1-acetyl-4-((5-chloropyrimidin-2-yl)amino)-2,3-dimethyl-1,2,3,4-tetrahydroquinoline-6-carboxylic acid (for a preparation see Intermediate 8, 150 mg, 0.400 mmol) and DIPEA (0.210 mL, 1.201 mmol) in DMF (2 mL) at rt under N$_2$. Following stirring at rt for 15 min, (R)-1-aminopropan-2-ol (60 mg, 0.799 mmol) was added in a single portion. The resultant solution was stirred at rt for 30 min. The DMF solution was then purified by MDAP. The appropriate fractions were combined and the solvent was evaporated under vacuum to give the product as a white solid (76 mg). LCMS (2 min Formic): Rt=0.82 min, [MH]$^+$=432.

Example 11

(2S,3R,4R)-1-acetyl-4-((5-cyanopyrazin-2-yl)amino)-2,3-dimethyl-1,2,3,4-tetrahydroquinoline-6-carboxamide

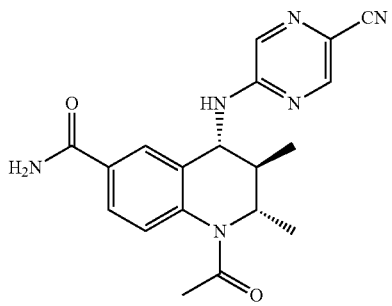

(2S,3R,4R)-1-acetyl-4-((5-cyanopyrazin-2-yl)amino)-2,3-dimethyl-1,2,3,4-tetrahydroquinoline-6-carboxylic acid (for a preparation see Intermediate 10, 72 mg, 0.197 mmol) was taken up in DMF (0.7 mL) and HATU (82 mg, 0.217 mmol) followed by DIPEA (0.069 mL, 0.394 mmol) was added. The reaction mixture was allowed to stir for 5 min, then ammonium chloride (21.08 mg, 0.394 mmol) was added and the reaction allowed to stir at rt for ~4 h. The reaction mixture was added directly to a vial and the flask washed with 2 portions of MeOH/DMSO (1:1, 0.2 mL). The vial was purified directly by MDAP. The appropriate fraction was collected and concentrated in vacuo to afford the product as a cream solid (32 mg). LCMS (2 min Formic): Rt=0.70 min, [MH]$^+$=365.

Example 12

(2S,3R,4R)-1-acetyl-4-((5-cyanopyrazin-2-yl)amino)-N-ethyl-2,3-dimethyl-1,2,3,4-tetrahydroquinoline-6-carboxamide

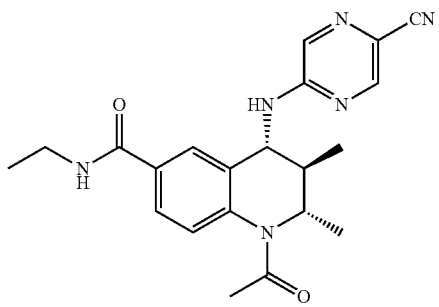 [SMILES: CCNC(=O)c1ccc2c(c1)[C@H](Nc1cnc(C#N)cn1)[C@@H](C)[C@H](C)N2C(C)=O]

(2S,3R,4R)-1-acetyl-4-((5-cyanopyrazin-2-yl)amino)-2,3-dimethyl-1,2,3,4-tetrahydroquinoline-6-carboxylic acid (for a preparation see Intermediate 10, 120 mg, 0.328 mmol) was taken up in DMF (1.4 mL) and HATU (137 mg, 0.361 mmol) followed by DIPEA (0.115 mL, 0.657 mmol) was added. The reaction mixture was allowed to stir for 5 min, then ethanamine (2M in THF) (0.328 mL, 0.657 mmol) was added and the reaction allowed to stir at rt for ~2.5 h. The reaction mixture was added directly to two vials and the flask washed with 2 portions of MeOH/DMSO (1:1, 0.2 mL). The vials were purified directly by MDAP. The appropriate fractions were collected and concentrated in vacuo to afford the product as a cream solid (58 mg). LCMS (2 min Formic): Rt=0.80 min, [MH]$^+$=393.

Example 13

(2S,3R,4R)-1-acetyl-N-ethyl-4-((5-fluoropyridin-2-yl)amino)-2,3-dimethyl-1,2,3,4-tetrahydroquinoline-6-carboxamide

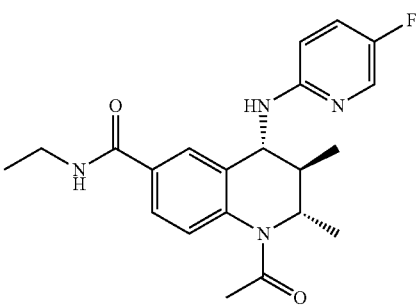 [SMILES: CCNC(=O)c1ccc2c(c1)[C@H](Nc1ccc(F)cn1)[C@@H](C)[C@H](C)N2C(C)=O]

(2S,3R,4R)-1-acetyl-4-((5-fluoropyridin-2-yl)amino)-2,3-dimethyl-1,2,3,4-tetrahydroquinoline-6-carboxylic acid (for a preparation see Intermediate 12, 30 mg, 0.084 mmol) was taken up in DMF (0.7 mL) and HATU (35.1 mg, 0.092 mmol) followed by DIPEA (0.029 mL, 0.168 mmol) was added. The reaction mixture was allowed to stir for 5 min, then ethanamine (2M in THF) (0.084 mL, 0.168 mmol) was added and the reaction allowed to stir at rt for ~1 h. The reaction mixture was added directly to a vial and the flask washed with 2 portions of MeOH/DMSO (1:1, 0.2 mL). The vial was purified directly by MDAP. The appropriate fractions were collected and concentrated in vacuo to afford the product as a cream solid (16 mg). LCMS (2 min Formic): Rt=0.71 min, [MH]$^+$=385.

Example 14

(2S,4R)-1-acetyl-4-((5-chloropyrimidin-2-yl)amino)-2-methyl-1,2,3,4-tetrahydroquinoline-6-carboxamide

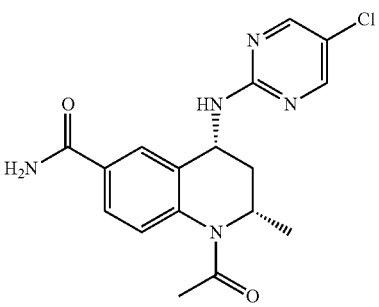 [SMILES: CC(=O)N1c2ccc(C(N)=O)cc2[C@H](Nc2ncc(Cl)cn2)C[C@@H]1C]

Hydrogen peroxide (0.12 mL, 35% by weight in H₂O, 1.40 mmol) was added dropwise over 30 s to a stirred suspension of (2S,4R)-1-acetyl-4-((5-chloropyrimidin-2-yl)amino)-2-methyl-1,2,3,4-tetrahydroquinoline-6-carbonitrile (for a preparation see Intermediate 15, 240 mg, 0.702 mmol) and potassium carbonate (388 mg, 2.81 mmol) in DMSO (5 mL) at rt under N₂. The resultant suspension was stirred at rt for 2 h. EtOAc (10 mL) and H₂O (10 mL) were added. The separated aqueous phase was extracted with EtOAc (2×10 mL), the combined organic phase was passed through a hydrophobic frit and evaporated under reduced pressure to give a pale yellow oil. The sample was loaded in DCM and purified by column chromatography (25 g silica) using a gradient of 0-100% EtOAc/cyclohexane and then 0-10% EtOH/EtOAc. The appropriate fractions were combined and evaporated under vacuum to give the product as a white solid (150 mg). LCMS (2 min Formic): Rt=0.71 min, [MH]⁺=360.

¹H NMR (400 MHz, d₆-DMSO) δ ppm 8.39 (br.s, 2H), 7.95 (d, J=8 Hz, 2H), 7.80 (dd, J=8, 2 Hz, 1H), 7.69 (s, 1H), 7.41 (d, J=8 Hz, 1H), 7.29 (br.s, 1H), 4.82 (ddd, J=12, 8, 4 Hz, 1H), 4.71-4.65 (m, 1H), 2.57-2.53 (m, 1H), 2.11 (s, 3H), 1.38 (td, J=13, 9 Hz, 1H), 1.08 (d, J=6 Hz, 3H). The enantiomeric excess (>99% ee) was determined by chiral HPLC analysis, 25 cm Chiralcel AD column, 40% EtOH/heptanes, 1 mL/min, wavelength 215 nm, room temperature, retention time=6.845 min.

Example 15

(2S,4R)-1-acetyl-4-((5-chloropyrimidin-2-yl)amino)-N-ethyl-2-methyl-1,2,3,4-tetrahydroquinoline-6-carboxamide

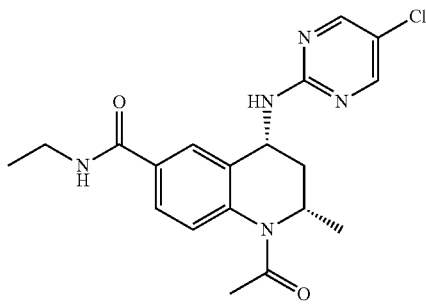 [SMILES: CCNC(=O)c1ccc2c(c1)[C@H](Nc1ncc(Cl)cn1)C[C@H](C)N2C(C)=O]

HATU (246 mg, 0.646 mmol) was added in a single portion to a stirred solution of (2S,4R)-1-acetyl-4-((5-chloropyrimidin-2-yl)amino)-2-methyl-1,2,3,4-tetrahydroquinoline-6-carboxylic acid (for a preparation see Intermediate 19, 212 mg, 0.588 mmol) and DIPEA (0.205 mL, 1.175 mmol) in DMF (5 mL) at rt under N₂. Following stirring at rt for 10 min, ethylamine (0.59 mL, 2 M in THF, 1.18 mmol) was added dropwise over 30 s. The resultant solution was stirred at rt for 16 h. EtOAc (10 mL) and H₂O (10 mL) were added. The separated aqueous phase was extracted with EtOAc (2×10 mL). The combined organic phase was passed through a hydrophobic frit and evaporated under reduced pressure to give a pale yellow oil. The sample was loaded in DCM and purified by column chromatography (25 g silica) using a gradient of 0-100% EtOAc/cyclohexane. The appropriate fractions were combined and evaporated under vacuum to give a yellow oil. The oil was dissolved in 1:1 MeOH:DMSO (3 mL) and purified by MDAP. The solvent was evaporated under vacuum to give the product as a white solid (67 mg). LCMS (2 min Formic): Rt=0.83 min, [MH]⁺=388.

Example 16

(2S,4R)-1-acetyl-4-((5-cyanopyridin-2-yl)amino)-N-ethyl-2-methyl-1,2,3,4-tetrahydroquinoline-6-carboxamide

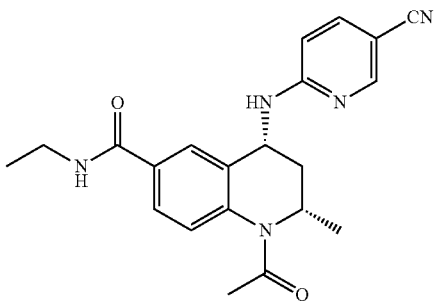 [SMILES: CCNC(=O)c1ccc2c(c1)[C@H](Nc1ccc(C#N)cn1)C[C@H](C)N2C(C)=O]

HATU (266 mg, 0.700 mmol) was added in a single portion to a stirred solution of (2S,4R)-1-acetyl-4-((5-cyanopyridin-2-yl)amino)-2-methyl-1,2,3,4-tetrahydroquinoline-6-carboxylic acid (for a preparation see Intermediate 22, 223 mg, 0.636 mmol) and DIPEA (0.222 mL, 1.273 mmol) in DMF (5 mL) at rt under N₂. Following stirring at rt for 10 min, ethylamine (0.64 mL, 2 M in THF, 1.27 mmol) was added dropwise over 30 s. The resultant solution was stirred at rt for 16 h. EtOAc (10 mL) and H₂O (10 mL) were added. The separated aqueous phase was extracted with EtOAc (2×10 mL). The combined organic phase was passed through a hydrophobic frit and evaporated under reduced pressure to give a pale yellow oil. The oil was dissolved in 1:1 MeOH:DMSO (3 mL) and purified by MDAP. The solvent was evaporated under vacuum to give the product as a white solid (106 mg). LCMS (2 min Formic): Rt=0.77 min, [MH]⁺=378.

Biological Test Methods

The compounds of formulae (I)-(XVI) may be tested in one or more of the following assays:

Time Resolved Fluorescence Resonance Energy Transfer (TR-FRET) Assay

Binding was assessed using a time resolved fluorescent resonance energy transfer binding assay. This utilises a 6 His purification tag at the N-terminal of the proteins as an epitope for an anti-6 His antibody labeled with Europium chelate (PerkinElmer AD0111) allowing binding of the Europium to the proteins which acts as the donor fluorophore. A small molecule, high affinity binder of the bromodomains BRD2, BRD3, BRD4 and BRDT has been labeled with Alexa Fluor647 (Reference Compound X) and this acts as the acceptor in the FRET pair.

Reference Compound X 4-((Z)-3-(6-((5-(2-((4S)-6-(4-chlorophenyl)-8-methoxy-1-methyl-4H-benzo[f][1,2,4]triazolo[4,3-a][1,4]diazepin-4-yl)acetamido)pentyl)amino)-6-oxohexyl)-2-((2E,4E)-5-(3,3-dimethyl-5-sulfo-1-(4-sulfobutyl)-3H-indol-1-ium-2-yl)penta-2,4-dien-1-ylidene)-3-methyl-5-sulfoindolin-1-yl)butane-1-sulphonate)

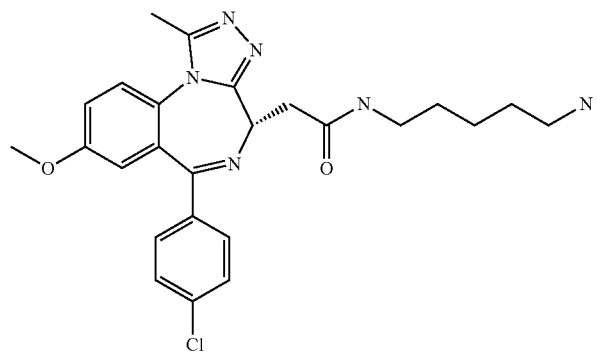

AF 647-NSu/DIPEA
DMF
⟶

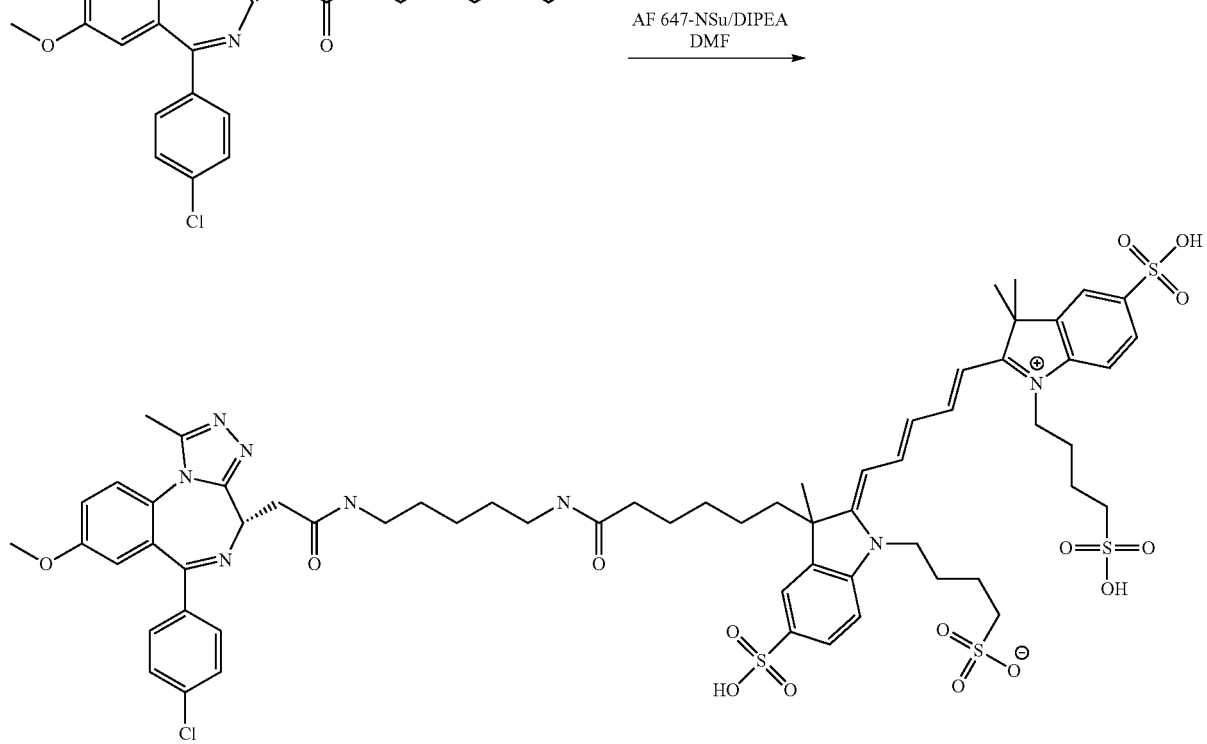

To a solution of N-(5-aminopentyl)-2-((4S)-6-(4-chlorophenyl)-8-methoxy-1-methyl-4H-benzo[f][1,2,4]triazolo[4,3-a][1,4]diazepin-4-yl)acetamide (for a preparation see Reference Compound J, WO2011/054848A1, 1.7 mg, 3.53 μmol) in DMF (40 μl) was added a solution of AlexaFluor647-ONSu (2.16 mg, 1.966 μmol) also in DMF (100 μl). The mixture was basified with DIPEA (1 μl, 5.73 μmol) and agitated overnight on a vortex mixer. The reaction mixture was evaporated to dryness. The solid was dissolved in acetonitrile/water/acetic acid (5/4/1, <1 ml) filtered and was applied to a Phenomenex Jupiter C18 preparative column and eluted with the following gradient (A=0.1% trifluoroacetic acid in water, B=0.1% TFA/90% acetonitrile/10% water): Flow rate=10 ml/min., AU=20/10 (214 nm):

5-35%, t=0 min: B=5%; t=10 min: B=5%; t=100 min: B=35%; t=115 min: B=100% (Sep. grad: 0.33%/min)

The major component was eluted over the range 26-28% B but appeared to be composed of two peaks. The middle fraction (F1.26) which should contain "both" components was analysed by analytical HPLC (Spherisorb ODS2, 1 to 35% over 60 min): single component eluting at 28% B. Fractions F1.25/26&27 were combined and evaporated to dryness. Transferred with DMF, evaporated to dryness, triturated with dry ether and the blue solid dried overnight at <0.2 mbar: 1.54 mg.

Analytical HPLC (Sphersisorb ODS2, 1 to 35% B over 60 min): MSM10520-1: [M+H]$^+$ (obs): 661.8/– corresponding with M-29. This equates to [(M+2H)/2]$^+$ for a calculated mass of 1320.984 which is M-29. This is a standard occurrence with the Alexa Fluor 647 dye and represents a theoretical loss of two methylene groups under the conditions of the mass spectrometer.

Assay Principle: In the absence of a competing compound, excitation of the Europium causes the donor to emit at λ618 nm which excites the Alexa labelled bromodomain binding compound leading to an increased energy transfer that is measurable at λ647 nM. In the presence of a sufficient concentration of a compound that can bind these proteins, the interaction is disrupted leading to a quantifiable drop in fluorescent resonance energy transfer.

The binding of the compounds of formulae (I)-(XVI) to Bromodomains BRD2, BRD3, BRD4 and BRDT was assessed using mutated proteins to detect differential binding to either Binding Domain 1 (BD1) or Binding Domain 2 (BD2) on the bromodomain. These single residue mutations in the acetyl lysine binding pocket greatly lower the affinity of the fluoroligand (Reference Compound X) for the mutated domain (>1000 fold selective for the non-mutated domain). Therefore in the final assay conditions, binding of the fluoroligand to the mutated domain cannot be detected and subsequently the assay is suitable to determine the binding of compounds to the single non-mutated bromodomain.

Protein production: Recombinant Human Bromodomains [(BRD2 (1-473) (Y113A) and (Y386A), BRD3 (1-435) (Y73A) and (Y348A) BRD4 (1-477) (Y97A) and (Y390A) and BRDT (1-397) (Y66A) and (Y309A)] were expressed in E. coli cells (in pET15b vector for BRD2/3/4 and in pET28a vector for BRDT) with a 6-His tag at the N-terminal. The His-tagged Bromodomain pellet was resuspended in 50 mM HEPES (pH7.5), 300 mM NaCl, 10 mM imidazole & 1 μl/ml protease inhibitor cocktail and extracted from the E. coli cells using sonication and purified using a nickel sepharose high performance column, the proteins were washed and then eluted with a linear gradient of 0-500 mM imidazole with buffer 50 mM HEPES (pH7.5), 150 mM NaCl, 500 mM imidazole, over 20 column volumes. Final purification was completed by Superdex 200 prep grade size exclusion column. Purified protein was stored at −80° C. in 20 mM HEPES pH 7.5 and 100 mM NaCl. Protein identity was confirmed by peptide mass fingerprinting and predicted molecular weight confirmed by mass spectrometry.

Protocol for Bromodomain BRD2, 3, 4 and T, BD1+BD2 mutant assays: All assay components were dissolved in buffer composition of 50 mM HEPES pH7.4, 50 mM NaCl, 5% Glycerol, 1 mM DTT and 1 mM CHAPS. The final concentration of bromodomain proteins were 10 nM and the Alexa Fluor647 ligand was at Kd. These components were premixed and 5 μl of this reaction mixture was added to all wells containing 50 nl of various concentrations of test compound or DMSO vehicle (0.5% DMSO final) in Greiner 384 well black low volume microtitre plates and incubated in dark for 30 minutes at rt. 5 μl of detection mixture containing 1.5 nM final concentration anti-6His Europium chelate was added to all wells and a further dark incubation of at least 30 minutes was performed. Plates were then read on the Envision platereader, (λex=317 nm, donor λem=615 nm; acceptor λem=665 nm; Dichroic LANCE dual). Time resolved fluorescent intensity measurements were made at both emission wavelengths and the ratio of acceptor/donor was calculated and used for data analysis. All data was normalized to the mean of 16 high (inhibitor control—Example 11 of WO 2011/054846A1) and 16 low (DMSO) control wells on each plate. A four parameter curve fit of the following form was then applied:

$$y=a+((b-a)/(1+(10\textasciicircum x/10\textasciicircum c)\textasciicircum d))$$

Where 'a' is the minimum, 'b' is the Hill slope, 'c' is the $pIC_{50}$ and 'd' is the maximum.

All of Examples 1-16 were tested in the above BRD4 assays and were found to have a $pIC_{50}$ in the range of 5.9-7.1 in the BRD4 BD1 assay and a $pIC_{50}$ in the range of 6.8-7.6 in the BRD4 BD2 assay.

Measurement of LPS Induced Secretion of MCP-1 from Whole Blood

Activation of monocytic cells by agonists of toll-like receptors such as bacterial lipopolysaccharide (LPS) results in production of key inflammatory mediators including MCP-1. Such pathways are widely considered to be central to the pathophysiology of a range of auto-immune and inflammatory disorders.

Blood is collected in a tube containing Sodium heparin (Leo Pharmaceuticals) (10 units of heparin/mL of bloodl). 96-well compound plates containing 1 μL test sample in 100% DMSO were prepared (two replicates on account of donor variability). 130 μL of whole blood was dispensed into each well of the 96-well compound plates and incubated for 30 min at 37° C., 5% $CO_2$. 10 μL of lipopolysaccharide made up in PBS (200 ng/mL final assay concentration) was added to each well of the compound plates. The plates were then lidded and placed in the humidified primary cell incubator for 18-24 hours at 37° C., 5% $CO_2$. 140 μL of PBS was added to all wells of the compound plates containing blood. The plates were then sealed and centrifugated for 10 mins at 2500 rpm. 20 μL of cell supernatant was placed in a 96-well MSD plate pre-coated with human MCP-1 capture antibody. The plates were sealed and placed on a shaker at 600 rpm for 2 hours (r.t). 20 μL of Anti-human MCP-1 antibody labelled with MSD SULFO-TAG™ reagent is added to each well of the MSD plate (stock 50× was diluted 1:50 with Diluent 100, final assay concentration is 1 μg/mL). The plates were then re-sealed and shaken for another hour before washing with PBS. 150 μL of 2×MSD Read Buffer T (stock 4×MSD Read Buffer T was diluted 50:50 with de-ionised water) was then added to each well and the plates read on the MSD Sector Imager 6000. Concentration response curves for each compound were generated from the data and an $IC_{50}$ value was calculated.

All of Examples 1-16 were tested in the above assay and were found to have a $pIC_{50}$ in the range of 6.2-7.8.

These data demonstrate that bromodomain inhibitors tested in the above whole blood assay inhibited the production of key inflammatory mediator MCP-1.

Measurement of LPS Induced Secretion of IL-6 from Whole Blood

Activation in whole blood of predominantly monocytic cells by agonists of toll-like receptors such as bacterial lipopolysaccharide (LPS) results in production of key inflammatory mediators, including IL-6. Such pathways are widely considered to be central to the pathophysiology of a range of auto-immune and inflammatory disorders.

Human Whole Blood from 2 donors (n=2) is collected using Sodium heparin as anti-coagulent (Wockhardt cat# FP1712) (10 units of heparin/mL of blood). Compounds were prepared as [10 mM] DMSO stocks and then diluted such that the top starting concentration was [1.4 mM] followed by 8×3-fold dilutions in DMSO. Final assay concentrations start at [10 μM] for all compounds. 1 μL diluted compound was added per well in a 96-well U bottom plate. 1 μL DMSO only was added to column 10 (+ve control) and 1-((2S,4R)-2-methyl-4-(phenylamino)-6-(4-(piperidin-1-ylmethyl)phenyl)-3,4-dihydroquinolin-1(2H)-yl)ethanone (for a preparation see Compound 28, J. Med. Chem. 2014, 57, 8111-8131, 1 μL, 1.4 mM) added to column 11 (−ve control). 130 μL of whole blood was dispensed into each well of the 96-well compound plates and incubated for 30 min at 37° C., 5% $CO_2$. 10 μl LPS (Salmonella typhosa Sigma cat# L6386) made up in RPMI1640 ([200 ng/mL] final assay conc.) was added to each well (including +ve and −ve columns). Plates were briefly shaken and then incubated overnight (22-24 h) at 37° C. 5% $CO_2$. The following day, 140 μL PBS was added to each well, the plates were sealed, shaken at 600 rpm for 5 min and then centrifuged at ×1350 g (2500 rpm) for 10 min. 100 μL plasma was carefully removed for analysis. Before analysis IL-6 was diluted 10-fold in PBS, in order to fit within the MSD standard curve. 25 μL of cell supernatant was placed in a 96-well MSD plate pre-coated with human IL-6 capture antibody. The plates were sealed and placed on a shaker at 600 rpm for 1.5 h (rt). 25 μL of Anti-human IL-6 antibody labelled with MSD SULFO-TAG™ reagent is added to each well of the MSD plate (stock 50× was diluted 1:50 with Diluent 100, final assay concentration is [1 μg/mL]). The plates were then re-sealed and shaken for another hour before washing 3× with PBS/Tween 20 [0.05%]. 150 µL of 2×MSD Read Buffer T (stock 4×MSD Read Buffer T was diluted 50:50 with de-ionised water) was then added to each well and the plates read on the MSD Sector Imager 6000. Concentration response curves for each compound were generated from the data using internal $XC_{50}$ analysis and an $IC_{50}$ value was calculated.

The compound of Example 14 was tested in the above assay and found to have a $pIC_{50}$: 6.7 (n=6)

Measurement of LPS Induced Secretion of TNFα from Whole Blood

Activation in whole blood of predominantly monocytic cells by agonists of toll-like receptors such as bacterial lipopolysaccharide (LPS) results in production of key inflammatory mediators, including TNFα. Such pathways are widely considered to be central to the pathophysiology of a range of auto-immune and inflammatory disorders.

Human Whole Blood from 2 donors (n=2) is collected using Sodium heparin as anti-coagulent (Wockhardt cat# FP1712) (10 units of heparin/mL of blood). Compounds were prepared as [10 mM] DMSO stocks and then diluted such that the top starting concentration was [1.4 mM] followed by 8×3-fold dilutions in DMSO. Final assay concentrations start at [10 µM] for all compounds. 1 µL diluted compound was added per well in a 96-well U bottom plate. 1 µL DMSO only was added to column 10 (+ve control) and 1-((2S,4R)-2-methyl-4-(phenylamino)-6-(4-(piperidin-1-ylmethyl)phenyl)-3,4-dihydroquinolin-1(2H)-yl)ethanone (for a preparation see Compound 28, *J. Med. Chem.* 2014, 57, 8111-8131, 1 µL, 1.4 mM) added to column 11 (−ve control). 130 µL of whole blood was dispensed into each well of the 96-well compound plates and incubated for 30 min at 37° C., 5% $CO_2$. 10 ul LPS (*Salmonella typhosa* Sigma cat# L6386) made up in RPMI1640 ([200 ng/mL] final assay conc.) was added to each well (including +ve and −ve columns). Plates were briefly shaken and then incubated overnight (22-24 h) at 37° C. 5% $CO_2$. The following day, 140 µL PBS was added to each well, the plates were sealed, shaken at 600 rpm for 5 min and then centrifuged at ×1350 g (2500 rpm) for 10 min. 100 µL plasma was carefully removed for analysis. Analysis of TNFα was carried out using neat plasma, in order to fit within the MSD standard curve. 25 µL of cell supernatant was placed in a 96-well MSD plate pre-coated with human TNFα capture antibody. The plates were sealed and placed on a shaker at 600 rpm for 1.5 hours (room temp.). 25 µL of Anti-human TNFα antibody labelled with MSD SULFO-TAG™ reagent is added to each well of the MSD plate (stock 50× was diluted 1:50 with Diluent 100, final assay concentration is [1 µg/mL]). The plates were then re-sealed and shaken for another hour before washing 3× with PBS/Tween 20 [0.05%]. 150 µL of 2×MSD Read Buffer T (stock 4×MSD Read Buffer T was diluted 50:50 with de-ionised water) was then added to each well and the plates read on the MSD Sector Imager 6000. Concentration response curves for each compound were generated from the data using internal $XC_{50}$ analysis and an $IC_{50}$ value was calculated.

The compound of Example 14 was tested in the above assay and found to have a $pIC_{50}$: 7.2 (n=4)

Lipopolysaccharide (LPS) Induced Interleukin-6 (IL-6) Production Mouse Assay

The compound was assayed for its ability to inhibit lipopolysaccharide (LPS) induced interleukin-6 (IL-6) production in mice. Male CD1 mice (Charles River Laboratories, 5 per group) received an intravenous challenge of LPS (100 µg/kg, L3192 *E coli* 0127:B8) 1 hour after oral administration of compound (in 1% (w/v) methylcellulose, aq 400). Serial blood samples were collected via teil vein up to 4 hours or via cardiac puncture at 6 hours (terminal sample) post oral drug administration and the serum harvested from the blood samples was frozen at −80° C. On the day of analysis, the serum was thawed to room temperature and levels of IL-6 were measured using single-spot cytokine assay plates (K152QXD) from Meso Scale Discovery (MSD, Gaithersburg, Md.). The levels of IL-6 were detected according to the manufacturer's protocol (MSD) and read on a SECTOR imager 6000 (MSD). The mean IL-6 Cmax and $AUC_{0-t}$ values were generated using WinNonlin Phoenix version 6.3 and the mean percent Cmax and $AUC_{0-t}$ IL-6 reduction following treatment with compound was calculated compared to the corresponding vehicle treated group. Levels of significance were calculated by analysis of variance (ANOVA) followed by Dunnett's multiple comparison t-test using Graphpad Prism version 5.04 (Graphpad Software, San Diego, Calif.). Statistical differences were determined as *P<0.05, **P<0.01. Results are shown in Table 1.

TABLE 1

Showing the efficacy of the compound of Example 14 in the LPS-induced IL-6 assay

| Parameter | Vehicle | Example 14 1 mg/kg | Example 14 3 mg/kg | Example 14 10 mg/kg |
| --- | --- | --- | --- | --- |
| IL-6 $C_{max}$ (ng/mL) | 687 | 291 | 357 | 258 |
| % reduction in IL-6 Cmax from vehicle | — | 58 | 48 | 62* |
| IL-6 $AUC_{0-t}$ (ng · h/mL) | 1091 | 554 | 495 | 563 |
| % reduction in IL-6 AUC from vehicle | — | 49* | 55** | 48* |

These data demonstrate that the compound tested in the above in vivo assay inhibits IL-6 production following an acute challenge and may therefore have utility in the treatment of inflammatory diseases or conditions.

Trinitrophenol-Keyhole Limpet Hemocyanin (TNP-KLH) Induced Immunoglobulin-1 (IgG1) Production Mouse Assay The compound was assayed for its ability to inhibit trinitrophenol-keyhole limpet hemocyanin (TNP-KLH) induced Immunoglobulin-1 (IgG1) production in mice. Male CD1 mice (Charles River Laboratories, 8 per group) received a single oral administration of compound (in 1% (w/v) methylcellulose, aq 400) either once every day (QD), once every other day (QOD) or once every 72 hours (QOED) over a 14 day dosing period. On day 1 of the study, each mouse received a single bolus intraperitoneal (ip) administration of TNP-KLH (100 µg/kg, T-5060-25, Lot #021562-06) 1 hour after oral administration of compound. Serial blood samples were collected at 1 hour post oral compound administration via tail veil on days 1, 4, 7, 9 and 11 or via cardiac puncture (terminal sample) on day 14 and the serum harvested from the blood samples was frozen at −80° C. On the day of analysis, the serum was thawed to room temperature and levels of IgG1 were measured using a TNP ELISA (developed in-house) and read on a SpectraMax 190 spectrophotometer (Molecular Devices, CA). The mean IgG1 values were generated and the mean percent IgG1 reduction on day 14 following treatment with compound was calculated compared to the corresponding vehicle treated group. Levels of significance were calculated by analysis of variance (ANOVA) followed by Dunnett's multiple comparison t-test using Graphpad Prism version 5.04 (Graphpad Software, San Diego, Calif.). Statistical differences were determined as ***P<0.01. Results are shown in Table 2.

TABLE 2

Showing the efficacy of the compound of Example 14 in the TNP-KLH-induced IgG1 production mouse assay

| | | Dose Group | | |
|---|---|---|---|---|
| Parameter | Vehicle | Example 14 30 mg/kg, QD | Example 14 30 mg/kg, QOD | Example 14 30 mg/kg, QOED |
| Day 14 IgG1 (ng/mL) | 5337 | 127 | 373 | 3162 |
| % reduction in IgG1 from vehicle | — | 98*** | 93*** | 41 |

These data demonstrate that, in this in vivo chronic inflammatory model, the tested compound may be suitable for both once daily or for intermittent dosing.

Cancer Cell Line Proliferation Assay

The impact of the compound of Examples 7 and 14 on cancer cell proliferation was determined using patient derived NUT midline carcinoma cells (11060), multiple myeloma cells (OPM-2, DSMZ) and biphenotypic B myelomonocytic leukaemia cells (MV-4-11, ATCC) in a 72 hour proliferation assay. 11060 and OPM-2 cells were maintained in RPMI 1640 medium (Invitrogen) supplemented with 10% HI-FBS (Heat-Inactivated Fetal Bovine Serum, Hyclone) and 2 mM L-glutamine (Invitrogen) at 37° C. and an atmosphere of 5% $CO_2$. MV-4-11 cells were maintained in IMDM media supplemented with 10% HI-FCS, 2 mM L-glutamine, 1× Non-essential amino acids (Invitrogen) and 1× sodium pyruvate (1 mM) (Invitrogen). Cells were diluted to $1.11 \times 10^5$ cells/mL and 90 μL/well plated into black sided, clear bottomed 96 well tissue culture plates (Corning), using growth media supplemented with penicillin/streptomycin (Invitrogen). Cells were incubated overnight at 37° C. and in one plate, ATP levels were measured using the CellTiter Glo assay (Promega) according to the manufacturer's instructions, to give a baseline reading (t=0). 3-fold serial dilutions of compounds ranging from 6 mM to 0.3 μM were prepared in 100% DMSO. The DMSO dilution series was diluted 20-fold in growth media before 10 μl of the resulting dilutions were added to the appropriate wells of the remaining cell plates. The final compound concentrations in the wells ranged from 30 μM to 1.5 nM in 0.5% DMSO. Cells were incubated with compounds for 72 hours before assaying for ATP content using CellTiter Glo (t=72). CellTiter Glo data from each t=72 time point was normalised to the relevant t=0 time point data, and expressed as % t=0. This data was analysed using GraphPad Prism V5.04 software with sigmoidal curve fitting (log(inhibitor) vs. response—variable slope (four parameters)), constraining the minimum value of the curve to values ≥100% to obtain $gpIC_{50}$ (growth $pIC_{50}$) values, whilst $pIC_{50}$ values were obtained from full curve fits, reported in Table 3.

TABLE 3

Showing the efficacy of the compound of Example 14 and the compound of Example 7 in cellular proliferation assay using 11060, MV-4-11 and OPM-2 cells

| | Example 14 | | Example 7 | |
|---|---|---|---|---|
| | Cellular Proliferation: $gpIC_{50}$ | Cellular Proliferation: $pIC_{50}$ | Cellular Proliferation: $gpIC_{50}$ | Cellular Proliferation: $pIC_{50}$ |
| 11060 (n = 3) | 6.2 | 6.0 | 6.4 | 6.2 |
| MV-4-11 (n = 3) | 6.6 | 6.5 | 6.8 | 6.7 |
| OPM-2 (n = 2) | 6.9 | 6.7 | 7.3 | 7.0 |

These data demonstrate that the compounds tested in the above assay inhibited cell growth in a range of oncology cell lines and may therefore have utility in the treatment of one or more cancers.

Mouse Xenograft Tumour Assay $1 \times 10^7$ NMC11060 cells, in 200 μl of 75% matrigel, were injected subcutaneously into each NOD/SCID mouse. Randomised oral administration of vehicle formulation, 1% Methycellulose (MC), or compound was initiated from the day tumour volume reached between 160-301 $mm^3$. Tumour volume was then measured every third day until either 21 days post inoculation or tumour volume had surpassed approximately 1000 $mm^3$. Results are shown in Table 4.

TABLE 4

Showing the efficacy of the compound of Example 14 in a NMC mouse xenograft assay

| Group | Treatment | Dose Group | Number of mice/group | % TGI |
|---|---|---|---|---|
| 1 | Vehicle | Vehicle | 7 | — |
| 2 | Compound of Example 14 | 10 mg/kg/day PO, QD for 21 days | 7 | 51* |
| 3 | Compound of Example 14 | 30 mg/kg/day PO, QD for 21 days | 7 | 93*** |

Tumour growth inhibition=100−mean tumor volume of treatment group/mean tumour volume of control group×100. P values are derived from coefficient of variation analysis using software PASS 12, comparing vehicle against drug treated group. Based on day 21,* p<0.05, p<0.01 and *p<0.001

These data further demonstrate the utility of the compound of Example 14 for use in the treatment of NUT-midline carcinoma.

All publications, including but not limited to patents and patent applications, cited in this specification are herein incorporated by reference as if each individual publication were specifically and individually indicated to be incorporated by reference herein as though fully set forth.

The invention claimed is:

1. A compound of formula (XIVa) which is (2S,4R)-1-acetyl-4-((5-chloropyrimidin-2-yl)amino)-2-methyl-1,2,3,4-tetrahydroquinoline-6-carboxamide

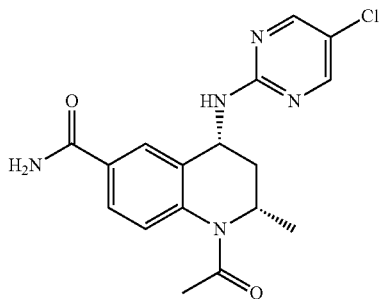

(XIVa)

or a pharmaceutically acceptable salt thereof.

2. The compound according to claim 1 in the form of a free base.

3. A pharmaceutical composition which comprises the compound or a pharmaceutically acceptable salt thereof according to claim 1 and one or more pharmaceutically acceptable carriers, diluents or excipients.

4. A method of treating diseases or conditions for which a bromodomain inhibitor is indicated in a human in need thereof, selected from the group consisting of an inflammatory condition, an inflammatory response to an infection with bacteria, a virus, fungi, a parasite or their toxins, a viral infection, and cancer, which comprises administering a therapeutically effective amount of the compound or a pharmaceutically acceptable salt thereof, according to claim 1.

5. A method of treatment according to claim 4, wherein the disease or condition is an inflammatory condition.

6. A method of treatment according to claim 4, wherein the disease or condition is cancer.

7. A method of treatment according to claim 4, wherein the disease or condition involves an inflammatory response to an infection with bacteria, a virus, fungi, a parasite or their toxins.

8. A method of treatment according to claim 4, wherein the disease or condition is a viral infection.

9. A method of treatment according to claim 5, wherein the inflammatory condition is rheumatoid arthritis.

10. A method of treatment according to claim 6, wherein the cancer is selected from hematological, lung, breast, colon, midline carcinomas, mesenchymal, hepatic, renal, and neurological tumors.

11. A pharmaceutical composition which comprises the compound or a pharmaceutically acceptable salt thereof according to claim 2 and one or more pharmaceutically acceptable carriers, diluents or excipients.

12. A method of treating diseases or conditions for which a bromodomain inhibitor is indicated in a human in need thereof, selected from the group consisting of an inflammatory condition, an inflammatory response to an infection with bacteria, a virus, fungi, a parasite or their toxins, a viral infection, and cancer, which comprises administering a therapeutically effective amount of the compound or a pharmaceutically acceptable salt thereof, according to claim 2.

13. A method of treatment according to claim 12, wherein the disease or condition is an inflammatory condition.

14. A method of treatment according to claim 12, wherein the disease or condition is cancer.

15. A method of treatment according to claim 12, wherein the disease or condition involves an inflammatory response to an infection with bacteria, a virus, fungi, a parasite or their toxins.

16. A method of treatment according to claim 12, wherein the disease or condition is a viral infection.

17. A method of treatment according to claim 13, wherein the inflammatory condition is rheumatoid arthritis.

18. A method of treatment according to claim 14, wherein the cancer is selected from hematological, lung, breast, colon, midline carcinomas, mesenchymal, hepatic, renal, and neurological tumors.

* * * * *